US008753631B2

(12) United States Patent
Karpatkin et al.

(10) Patent No.: US 8,753,631 B2
(45) Date of Patent: Jun. 17, 2014

(54) THERAPEUTIC AGENTS FOR INDUCING PLATELET FRAGMENTATION AND TREATING THROMBOEMBOLIC DISORDERS

(75) Inventors: Simon Karpatkin, New York, NY (US); Michael Nardi, New York, NY (US); Zongdong Li, New York, NY (US)

(73) Assignee: New York University, New York, NY (US)

(*) Notice: Subject to any disclaimer, the term of this patent is extended or adjusted under 35 U.S.C. 154(b) by 45 days.

(21) Appl. No.: 12/771,492

(22) Filed: Apr. 30, 2010

(65) Prior Publication Data

US 2011/0045008 A1 Feb. 24, 2011

Related U.S. Application Data

(60) Provisional application No. 61/174,620, filed on May 1, 2009.

(51) Int. Cl.
*A61K 39/395* (2006.01)
*C07K 16/28* (2006.01)
*C07K 19/00* (2006.01)
*C07K 14/745* (2006.01)

(52) U.S. Cl.
CPC ............. *C07K 16/2848* (2013.01); *C07K 19/00* (2013.01); *C07K 14/745* (2013.01); *C07K 2317/622* (2013.01); *C07K 2319/01* (2013.01); *C07K 2319/33* (2013.01); *A61K 39/3955* (2013.01)
USPC .................. 424/139.1; 424/134.1; 424/135.1; 424/143.1; 424/153.1; 424/192.1; 530/387.3; 530/387.9; 530/388.22; 530/388.7; 530/350; 514/13.8; 514/13.9; 514/14.9

(58) Field of Classification Search
None
See application file for complete search history.

(56) References Cited

U.S. PATENT DOCUMENTS

| | | | | |
|---|---|---|---|---|
| 5,610,171 | A | 3/1997 | Bitonti | |
| 5,777,085 | A | 7/1998 | Co et al. | |
| 5,877,305 | A * | 3/1999 | Huston et al. | 536/23.53 |
| 5,976,532 | A | 11/1999 | Coller et al. | |
| 6,585,995 | B1 | 7/2003 | Hanson | |
| 2004/0044194 | A1 | 3/2004 | Corcoran et al. | |
| 2004/0236079 | A1 * | 11/2004 | Karpatkin et al. | 530/388.22 |
| 2011/0052594 | A1 | 3/2011 | Karpatkin et al. | |

FOREIGN PATENT DOCUMENTS

| | | |
|---|---|---|
| WO | WO 2005085468 A1 * | 9/2005 |
| WO | WO 2005103287 A1 * | 11/2005 |

OTHER PUBLICATIONS

Li et al., Blood. Jun. 11, 2009;113(24):6051-60. doi: 10.1182/blood-2008-07-170571. Epub Feb. 13, 2009.*

Boyland et al., Blood. Oct. 1, 2008;112(7):2780-6. doi: 10.1182/blood-2008-02-142125. Epub Jul. 18, 2008.*

Cazenave et al., "Anti-platelet Drugs: Do they Affect Megakaryocytes?," Baillieres Clinical Haematology, 10(1):163-80 (1997).

Harlow et al., "Antibodies A Laboratory Manual," Cold Spring Harbor, New York, Cold Spring Harbor Laboratory Press (1988).

Warkentin, "Heparin-Induced Thrombocytopenia: Pathogenesis and Management," British Journal of Haematology, 121(4):535-55 (2003).

Said et al., "Glycoprotein IIb/IIIa Inhibitor-induced Thrombocytopenia," Clin. Res. Cardiol. 96:61-69 (2007).

Aster et al., "Thrombocytopenia Associated with the Use of GPIIb/IIIa Inhibitors: Position Paper of the ISTH Working Group on Thrombocytopenia and GPIIb/IIIa Inhibitors," J. Thrombo. Haemostasis 4:678-679 (2006).

Brass, L.F. "Thrombin and Platelet Activation," Chest 124:18S-25S (2003).

Zhang et al., "Dissolution of Arterial Platelet Thrombi in vivo with Bifunctional Platelet GPIIIa49-66 Ligand Which Specifically Targets the Platelet Thrombus," Blood 116:2336-2344 (2010).

Collen and Lijnen, "Thrombolytic Agents," Thromb. Haemost. 93:627-630 (2005).

Novokhatny, "Structure and Activity of Plasmin and Other Direct Thrombolytic Agents," Thrombosis Res. 122:S3-S8 (2008).

Huang et al., "Trigramin: A Low Molecular Weight Peptide Inhibiting Fibrinogen Interaction With Platelet Receptors Expressed on Glycoprotein IIB-IIIa Complex," J. Biol. Chem. 262(33):16157-16163 (1987) (Abstract).

Nardi et al., "Autoimmune Anti-GPIIIa Ab Induces Platelet Lysis in the Absence of Complement in HIV-1-Related Immunologic Thrombocytopenia (HIV-1-ITP)," Blood 96(11)Pt.1:248a (2000) (Abstract).

Nardi et al., "Platelet Particle Formation by Anti GPIIIa49-66 Ab, Ca2+ Ionophore A23187, and Phorbol Myristate Acetate is Induced by Reactive Oxygen Species and Inhibited by Dexamethasone Blockage of Platelet Phospholipase A 2, 12-lipoxygenase, and NADPH Oxidase," Blood 110:1989-1996 (2007).

Nardi et al., "Complement-independent Ab-induced Peroxide Lysis of Platelets Requires 12-lipoxygenase and a Platelet NADPH Oxidase Pathway," The Journal of Clinical Investigation 113:973-980 (2004).

Li et al., "A New Mechanism of Platelet Activation, Oxidation and Death Induced by ADAMTS-18," Blood 106 (2005) (Abstract).

Nardi et al., "GPIIIa-(49-66) is a Major Pathophysiologically Relevant Antigenic Determinant for Anti-platelet GPIIIa of HIV-1-related Immunologic Thrombocytopenia," Proc. Natl. Acad. Sci. USA 94:7589-7594 (1997).

Li et al., "Platelet Fragmentation Requires a Specific Structural Conformation of Human Monoclonal Antibody Against Beta3 Integrin," The Journal of Biological Chemistry 283(6):3224-3230 (2008).

Nardi et al., "Complement-independent, Peroxide-induced Antibody Lysis of Platelets in HIV-1-related Immune Thrombocytopenia," Cell 106:551-561 (2001).

Li et al., "C-terminal ADAMTS-18 Fragment Induces Oxidative Platelet Fragmentation, Dissolves Platelet Aggregates and Protects Against Carotid Artery Occlusion and Cerebral Stroke," Blood 113(24):6051-6060 (2009).

* cited by examiner

*Primary Examiner* — Michael Szperka
(74) *Attorney, Agent, or Firm* — LeClairRyan, a Professional Corporation

(57) ABSTRACT

The present invention is directed to a therapeutic agent comprising a GPIIIa(49-66) specific targeting agent and a thrombi-specific homing agent. Also disclosed is the use of the therapeutic agent in carrying out a method of treating thromboembolic disorders and a method of inducing platelet fragmentation.

21 Claims, 16 Drawing Sheets

FIGURE 3

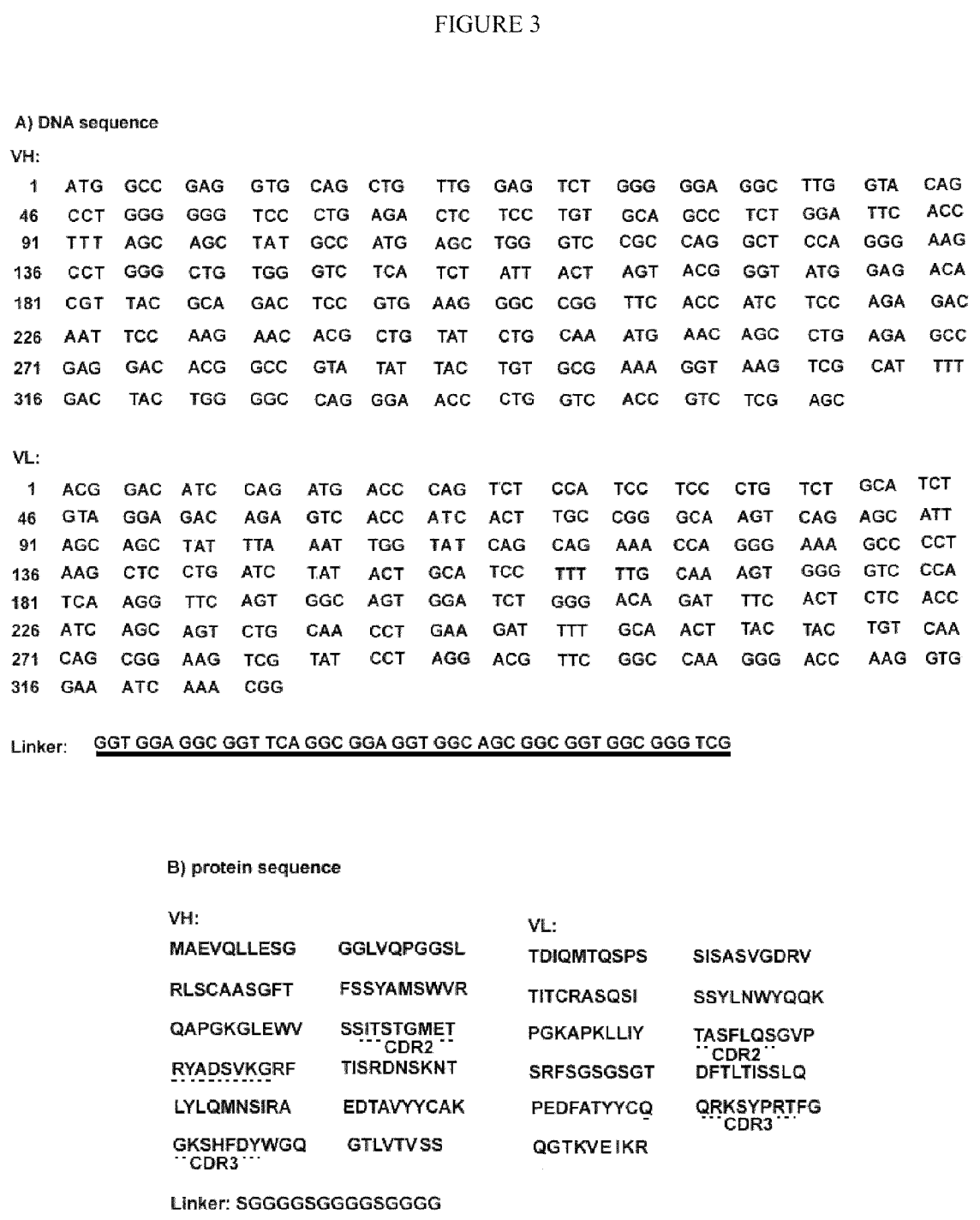

A) DNA sequence

VH:

1 ATG GCC GAG GTG CAG CTG TTG GAG TCT GGG GGA GGC TTG GTA CAG
46 CCT GGG GGG TCC CTG AGA CTC TCC TGT GCA GCC TCT GGA TTC ACC
91 TTT AGC AGC TAT GCC ATG AGC TGG GTC CGC CAG GCT CCA GGG AAG
136 CCT GGG CTG TGG GTC TCA TCT ATT ACT AGT ACG GGT ATG GAG ACA
181 CGT TAC GCA GAC TCC GTG AAG GGC CGG TTC ACC ATC TCC AGA GAC
226 AAT TCC AAG AAC ACG CTG TAT CTG CAA ATG AAC AGC CTG AGA GCC
271 GAG GAC ACG GCC GTA TAT TAC TGT GCG AAA GGT AAG TCG CAT TTT
316 GAC TAC TGG GGC CAG GGA ACC CTG GTC ACC GTC TCG AGC

VL:

1 ACG GAC ATC CAG ATG ACC CAG TCT CCA TCC TCC CTG TCT GCA TCT
46 GTA GGA GAC AGA GTC ACC ATC ACT TGC CGG GCA AGT CAG AGC ATT
91 AGC AGC TAT TTA AAT TGG TAT CAG CAG AAA CCA GGG AAA GCC CCT
136 AAG CTC CTG ATC TAT ACT GCA TCC TTT TTG CAA AGT GGG GTC CCA
181 TCA AGG TTC AGT GGC AGT GGA TCT GGG ACA GAT TTC ACT CTC ACC
226 ATC AGC AGT CTG CAA CCT GAA GAT TTT GCA ACT TAC TAC TGT CAA
271 CAG CGG AAG TCG TAT CCT AGG ACG TTC GGC CAA GGG ACC AAG GTG
316 GAA ATC AAA CGG

Linker: GGT GGA GGC GGT TCA GGC GGA GGT GGC AGC GGC GGT GGC GGG TCG

B) protein sequence

VH:

MAEVQLLESG GGLVQPGGSL
RLSCAASGFT FSSYAMSWVR
QAPGKGLEWV SSITSTGMET
CDR2
RYADSVKGRF TISRDNSKNT
LYLQMNSIRA EDTAVYYCAK
GKSHFDYWGQ GTLVTVSS
CDR3

Linker: SGGGGSGGGGSGGGG

VL:

TDIQMTQSPS SISASVGDRV
TITCRASQSI SSYLNWYQQK
PGKAPKLLIY TASFLQSGVP
CDR2
SRFSGSGSGT DFTLTISSLQ
PEDFATYYCQ QRKSYPRTFG
CDR3
QGTKVEIKR

FIGURE 9
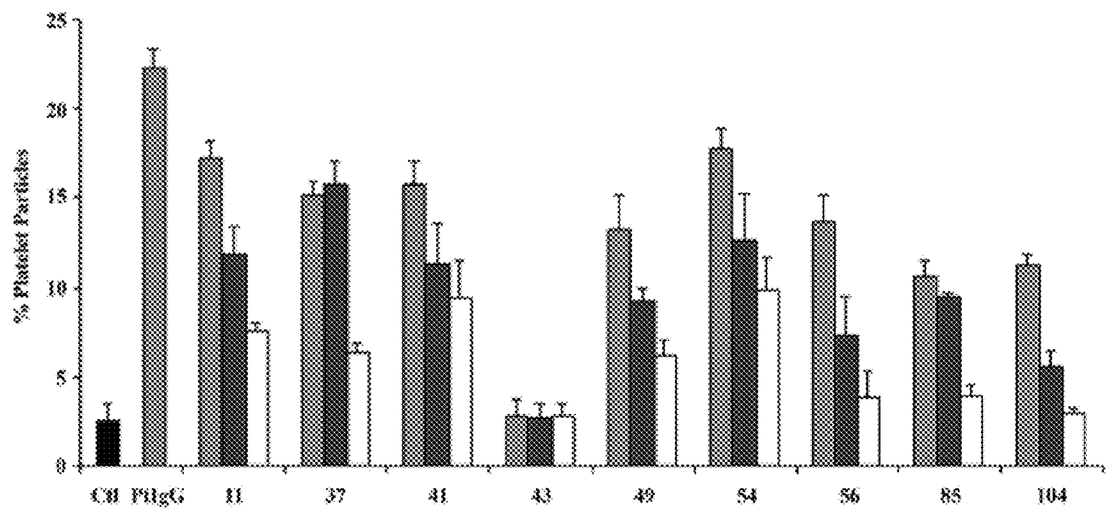
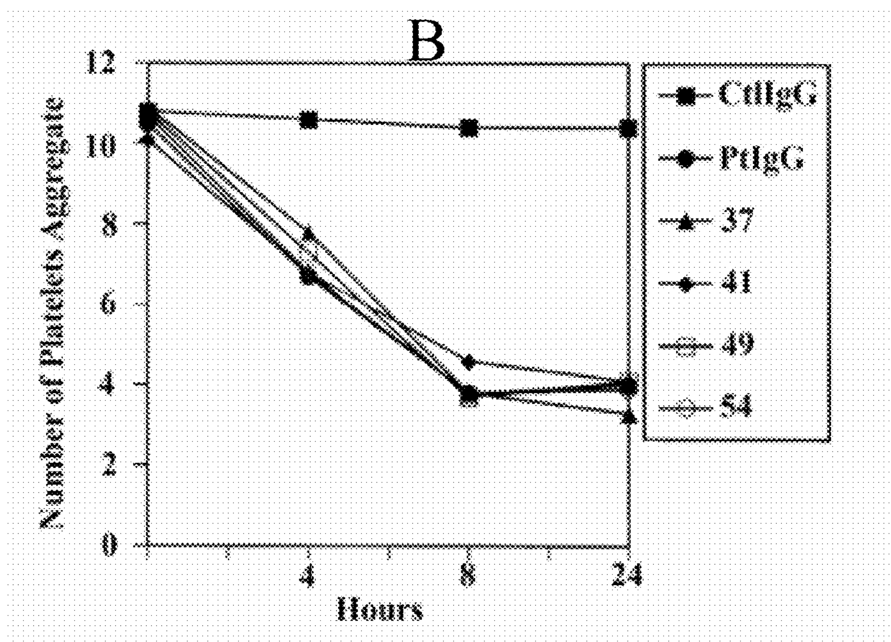

SEQUENCE LISTING

```
<160> NUMBER OF SEQ ID NOS: 32

<210> SEQ ID NO 1
<211> LENGTH: 354
<212> TYPE: DNA
<213> ORGANISM: Homo sapiens

<400> SEQUENCE: 1

atggccgagg tgcagctgtt ggagtctggg ggaggcttgg tacagcctgg ggggtccctg     60

agactctcct gtgcagcctc tggattcacc tttagcagct atgccatgag ctgggtccgc    120

caggctccag ggaagcctgg gctgtgggtc tcatctatta ctagtacggg tatggagaca    180

cgttacgcag actccgtgaa gggccggttc accatctcca gagacaattc caagaacacg    240
```

```
ctgtatctgc aaatgaacag cctgagagcc gaggacacgg ccgtatatta ctgtgcgaaa    300

ggtaagtcgc attttgacta ctggggccag ggaaccctgg tcaccgtctc gagc          354


<210> SEQ ID NO 2
<211> LENGTH: 327
<212> TYPE: DNA
<213> ORGANISM: Homo sapiens

<400> SEQUENCE: 2

acggacatcc agatgaccca gtctccatcc tccctgtctg catctgtagg agacagagtc     60

accatcactt gccgggcaag tcagagcatt agcagctatt taaattggta tcagcagaaa    120

ccagggaaag cccctaagct cctgatctat actgcatcct tttgcaaag tggggtccca     180

tcaaggttca gtggcagtgg atctgggaca gatttcactc tcaccatcag cagtctgcaa    240

cctgaagatt ttgcaactta ctactgtcaa cagcggaagt cgtatcctag gacgttcggc    300

caagggacca aggtggaaat caaacgg                                        327


<210> SEQ ID NO 3
<211> LENGTH: 45
<212> TYPE: DNA
<213> ORGANISM: Artificial
<220> FEATURE:
<223> OTHER INFORMATION: linker

<400> SEQUENCE: 3

ggtggaggcg gttcaggcgg aggtggcagc ggcggtggcg ggtcg                     45


<210> SEQ ID NO 4
<211> LENGTH: 118
<212> TYPE: PRT
<213> ORGANISM: Homo sapiens

<400> SEQUENCE: 4

Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ser Ile Thr Ser Thr Gly Met Glu Thr Arg Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Ile Arg Ala Glu Asp Thr Ala Val Tyr
                85                  90                  95

Tyr Cys Ala Lys Gly Lys Ser His Phe Asp Tyr Trp Gly Gln Gly Thr
            100                 105                 110

Leu Val Thr Val Ser Ser
        115


<210> SEQ ID NO 5
<211> LENGTH: 109
<212> TYPE: PRT
<213> ORGANISM: Homo sapiens

<400> SEQUENCE: 5

Thr Asp Ile Gln Met Thr Gln Ser Pro Ser Ser Ile Ser Ala Ser Val
1               5                   10                  15

Gly Asp Arg Val Thr Ile Thr Cys Arg Ala Ser Gln Ser Ile Ser Ser
```

```
            20                  25                  30

Tyr Leu Asn Trp Tyr Gln Gln Lys Pro Gly Lys Ala Pro Lys Leu Leu
        35                  40                  45

Ile Tyr Thr Ala Ser Phe Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Arg Lys Ser Tyr Pro
                85                  90                  95

Arg Thr Phe Gly Gln Gly Thr Lys Val Glu Ile Lys Arg
            100                 105


<210> SEQ ID NO 6
<211> LENGTH: 15
<212> TYPE: PRT
<213> ORGANISM: Artificial
<220> FEATURE:
<223> OTHER INFORMATION: linker

<400> SEQUENCE: 6

Ser Gly Gly Gly Gly Ser Gly Gly Gly Gly Ser Gly Gly Gly Gly
1               5                   10                  15


<210> SEQ ID NO 7
<211> LENGTH: 6
<212> TYPE: PRT
<213> ORGANISM: Artificial
<220> FEATURE:
<223> OTHER INFORMATION: PAR-1 agonist

<400> SEQUENCE: 7

Thr Phe Leu Leu Arg Asn
1               5


<210> SEQ ID NO 8
<211> LENGTH: 18
<212> TYPE: PRT
<213> ORGANISM: Artificial
<220> FEATURE:
<223> OTHER INFORMATION: 18-mer peptide

<400> SEQUENCE: 8

Val Gln Thr Arg Ser Val His Cys Val Gln Gln Gly Arg Pro Ser Ser
1               5                   10                  15

Ser Cys


<210> SEQ ID NO 9
<211> LENGTH: 18
<212> TYPE: PRT
<213> ORGANISM: Homo sapiens

<400> SEQUENCE: 9

Cys Ala Pro Glu Ser Ile Glu Phe Pro Val Ser Glu Ala Arg Val Leu
1               5                   10                  15

Glu Asp


<210> SEQ ID NO 10
<211> LENGTH: 384
<212> TYPE: PRT
<213> ORGANISM: Homo sapiens

<400> SEQUENCE: 10

Asn Glu Thr Leu Val Phe Glu Ile Leu Met Gln Gly Lys Asn Pro Gly
```

```
1               5                   10                  15

Ile Ala Trp Lys Tyr Ala Leu Pro Lys Val Met Asn Gly Thr Pro Pro
            20                  25                  30

Ala Thr Lys Arg Pro Ala Tyr Thr Trp Ser Ile Val Gln Ser Glu Cys
        35                  40                  45

Ser Val Ser Cys Gly Gly Gly Tyr Ile Asn Val Lys Ala Ile Cys Leu
    50                  55                  60

Arg Asp Gln Asn Thr Gln Val Asn Ser Ser Phe Cys Ser Ala Lys Thr
65                  70                  75                  80

Lys Pro Val Thr Glu Pro Lys Ile Cys Asn Ala Phe Ser Cys Pro Ala
                85                  90                  95

Tyr Trp Met Pro Gly Glu Trp Ser Thr Cys Ser Lys Ala Cys Ala Gly
            100                 105                 110

Gly Gln Gln Ser Arg Lys Ile Gln Cys Val Gln Lys Lys Pro Phe Gln
        115                 120                 125

Lys Glu Glu Ala Val Leu His Ser Leu Cys Pro Val Ser Thr Pro Thr
    130                 135                 140

Gln Val Gln Ala Cys Asn Ser His Ala Cys Pro Pro Gln Trp Ser Leu
145                 150                 155                 160

Gly Pro Trp Ser Gln Cys Ser Lys Thr Cys Gly Arg Gly Val Arg Lys
                165                 170                 175

Arg Glu Leu Leu Cys Lys Gly Ser Ala Ala Glu Thr Leu Pro Glu Ser
            180                 185                 190

Gln Cys Thr Ser Leu Pro Arg Pro Glu Leu Gln Glu Gly Cys Val Leu
        195                 200                 205

Gly Arg Cys Pro Lys Asn Ser Arg Leu Gln Trp Val Ala Ser Ser Trp
    210                 215                 220

Ser Glu Cys Ser Ala Thr Cys Gly Leu Gly Val Arg Lys Arg Glu Met
225                 230                 235                 240

Lys Cys Ser Glu Lys Gly Phe Gln Gly Lys Leu Ile Thr Phe Pro Glu
                245                 250                 255

Arg Arg Cys Arg Asn Ile Lys Lys Pro Asn Leu Asp Leu Glu Glu Thr
            260                 265                 270

Cys Asn Arg Arg Ala Cys Pro Ala His Pro Val Tyr Asn Met Val Ala
        275                 280                 285

Gly Trp Tyr Ser Leu Pro Trp Gln Gln Cys Thr Val Thr Cys Gly Gly
    290                 295                 300

Gly Val Gln Thr Arg Ser Val His Cys Val Gln Gln Gly Arg Pro Ser
305                 310                 315                 320

Ser Ser Cys Leu Leu His Gln Lys Pro Pro Val Leu Arg Ala Cys Asn
                325                 330                 335

Thr Asn Phe Cys Pro Ala Pro Glu Lys Arg Glu Asp Pro Ser Cys Val
            340                 345                 350

Asp Phe Phe Asn Trp Cys His Leu Val Pro Gln His Gly Val Cys Asn
        355                 360                 365

His Lys Phe Tyr Gly Lys Gln Cys Cys Lys Ser Cys Thr Arg Lys Ile
    370                 375                 380
```

<210> SEQ ID NO 11
<211> LENGTH: 1221
<212> TYPE: PRT
<213> ORGANISM: Homo sapiens

<400> SEQUENCE: 11

```
Met Glu Cys Ala Leu Leu Leu Ala Cys Ala Phe Pro Ala Ala Gly Ser
```

```
1               5                   10                  15

Gly Pro Pro Arg Gly Leu Ala Gly Leu Gly Arg Val Ala Lys Ala Leu
            20                  25                  30

Gln Leu Cys Cys Leu Cys Cys Ala Ser Val Ala Ala Ala Leu Ala Ser
        35                  40                  45

Asp Ser Ser Ser Gly Ala Ser Gly Leu Asn Asp Asp Tyr Val Phe Val
    50                  55                  60

Thr Pro Val Glu Val Asp Ser Ala Gly Ser Tyr Ile Ser His Asp Ile
65                  70                  75                  80

Leu His Asn Gly Arg Lys Lys Arg Ser Ala Gln Asn Ala Arg Ser Ser
                85                  90                  95

Leu His Tyr Arg Phe Ser Ala Phe Gly Gln Glu Leu His Leu Glu Leu
            100                 105                 110

Lys Pro Ser Ala Ile Leu Ser Ser His Phe Ile Val Gln Val Leu Gly
        115                 120                 125

Lys Asp Gly Ala Ser Glu Thr Gln Lys Pro Glu Val Gln Gln Cys Phe
    130                 135                 140

Tyr Gln Gly Phe Ile Arg Asn Asp Ser Ser Ser Ser Val Ala Val Ser
145                 150                 155                 160

Thr Cys Ala Gly Leu Ser Gly Leu Ile Arg Thr Arg Lys Asn Glu Phe
                165                 170                 175

Leu Ile Ser Pro Leu Pro Gln Leu Leu Ala Gln Glu His Asn Tyr Ser
            180                 185                 190

Ser Pro Ala Gly His His Pro His Val Leu Tyr Lys Arg Thr Ala Glu
        195                 200                 205

Glu Lys Ile Gln Arg Tyr Arg Gly Tyr Pro Gly Ser Gly Arg Asn Tyr
    210                 215                 220

Pro Gly Tyr Ser Pro Ser His Ile Pro His Ala Ser Gln Ser Arg Glu
225                 230                 235                 240

Thr Glu Tyr His His Arg Arg Leu Gln Lys Gln His Phe Cys Gly Arg
                245                 250                 255

Arg Lys Lys Tyr Ala Pro Lys Pro Pro Thr Glu Asp Thr Tyr Leu Arg
            260                 265                 270

Phe Asp Glu Tyr Gly Ser Ser Gly Arg Pro Arg Arg Ser Ala Gly Lys
        275                 280                 285

Ser Gln Lys Gly Leu Asn Val Glu Thr Leu Val Val Ala Asp Lys Lys
    290                 295                 300

Met Val Glu Lys His Gly Lys Gly Asn Val Thr Thr Tyr Ile Leu Thr
305                 310                 315                 320

Val Met Asn Met Val Ser Gly Leu Phe Lys Asp Gly Thr Ile Gly Ser
                325                 330                 335

Asp Ile Asn Val Val Val Val Ser Leu Ile Leu Leu Glu Gln Glu Pro
            340                 345                 350

Gly Gly Leu Leu Ile Asn His His Ala Asp Gln Ser Leu Asn Ser Phe
        355                 360                 365

Cys Gln Trp Gln Ser Ala Leu Ile Gly Lys Asn Gly Lys Arg His Asp
    370                 375                 380

His Ala Ile Leu Leu Thr Gly Phe Asp Ile Cys Ser Trp Lys Asn Glu
385                 390                 395                 400

Pro Cys Asp Thr Leu Gly Phe Ala Pro Ile Ser Gly Met Cys Ser Lys
                405                 410                 415

Tyr Arg Ser Cys Thr Ile Asn Glu Asp Thr Gly Leu Gly Leu Ala Phe
            420                 425                 430
```

```
Thr Ile Ala His Glu Ser Gly His Asn Phe Gly Met Ile His Asp Gly
        435                 440                 445

Glu Gly Asn Pro Cys Arg Lys Ala Glu Gly Asn Ile Met Ser Pro Thr
    450                 455                 460

Leu Thr Gly Asn Asn Gly Val Phe Ser Trp Ser Ser Cys Ser Arg Gln
465                 470                 475                 480

Tyr Leu Lys Lys Phe Leu Ser Thr Pro Gln Ala Gly Cys Leu Val Asp
                485                 490                 495

Glu Pro Lys Gln Ala Gly Gln Tyr Lys Tyr Pro Asp Lys Leu Pro Gly
            500                 505                 510

Gln Ile Tyr Asp Ala Asp Thr Gln Cys Lys Trp Gln Phe Gly Ala Lys
        515                 520                 525

Ala Lys Leu Cys Ser Leu Gly Phe Val Lys Asp Ile Cys Lys Ser Leu
    530                 535                 540

Trp Cys His Arg Val Gly His Arg Cys Glu Thr Lys Phe Met Pro Ala
545                 550                 555                 560

Ala Glu Gly Thr Val Cys Gly Leu Ser Met Trp Cys Arg Gln Gly Gln
                565                 570                 575

Cys Val Lys Phe Gly Glu Leu Gly Pro Arg Pro Ile His Gly Gln Trp
            580                 585                 590

Ser Ala Trp Ser Lys Trp Ser Glu Cys Ser Arg Thr Cys Gly Gly Gly
        595                 600                 605

Val Lys Phe Gln Glu Arg His Cys Asn Asn Pro Lys Pro Gln Tyr Gly
    610                 615                 620

Gly Leu Phe Cys Pro Gly Ser Ser Arg Ile Tyr Gln Leu Cys Asn Ile
625                 630                 635                 640

Asn Pro Cys Asn Glu Asn Ser Leu Asp Phe Arg Ala Gln Gln Cys Ala
                645                 650                 655

Glu Tyr Asn Ser Lys Pro Phe Arg Gly Trp Phe Tyr Gln Trp Lys Pro
            660                 665                 670

Tyr Thr Lys Val Glu Glu Glu Asp Arg Cys Lys Leu Tyr Cys Lys Ala
        675                 680                 685

Glu Asn Phe Glu Phe Phe Phe Ala Met Ser Gly Lys Val Lys Asp Gly
    690                 695                 700

Thr Pro Cys Ser Pro Asn Lys Asn Asp Val Cys Ile Asp Gly Val Cys
705                 710                 715                 720

Glu Leu Val Gly Cys Asp His Glu Leu Gly Ser Lys Ala Val Ser Asp
                725                 730                 735

Ala Cys Gly Val Cys Lys Gly Asp Asn Ser Thr Cys Lys Phe Tyr Lys
            740                 745                 750

Gly Leu Tyr Leu Asn Gln His Lys Ala Asn Glu Tyr Tyr Pro Val Val
        755                 760                 765

Leu Ile Pro Ala Gly Ala Arg Ser Ile Glu Ile Gln Glu Leu Gln Val
    770                 775                 780

Ser Ser Ser Tyr Leu Ala Val Arg Ser Leu Ser Gln Lys Tyr Tyr Leu
785                 790                 795                 800

Thr Gly Gly Trp Ser Ile Asp Trp Pro Gly Glu Phe Pro Phe Ala Gly
                805                 810                 815

Thr Thr Phe Glu Tyr Gln Arg Ser Phe Asn Arg Pro Glu Arg Leu Tyr
            820                 825                 830

Ala Pro Gly Pro Thr Asn Glu Thr Leu Val Phe Glu Ile Leu Met Gln
        835                 840                 845

Gly Lys Asn Pro Gly Ile Ala Trp Lys Tyr Ala Leu Pro Lys Val Met
    850                 855                 860
```

```
Asn Gly Thr Pro Pro Ala Thr Lys Arg Pro Ala Tyr Thr Trp Ser Ile
865                 870                 875                 880

Val Gln Ser Glu Cys Ser Val Ser Cys Gly Gly Gly Tyr Ile Asn Val
                885                 890                 895

Lys Ala Ile Cys Leu Arg Asp Gln Asn Thr Gln Val Asn Ser Ser Phe
            900                 905                 910

Cys Ser Ala Lys Thr Lys Pro Val Thr Glu Pro Lys Ile Cys Asn Ala
        915                 920                 925

Phe Ser Cys Pro Ala Tyr Trp Met Pro Gly Glu Trp Ser Thr Cys Ser
    930                 935                 940

Lys Ala Cys Ala Gly Gly Gln Gln Ser Arg Lys Ile Gln Cys Val Gln
945                 950                 955                 960

Lys Lys Pro Phe Gln Lys Glu Glu Ala Val Leu His Ser Leu Cys Pro
                965                 970                 975

Val Ser Thr Pro Thr Gln Val Gln Ala Cys Asn Ser His Ala Cys Pro
            980                 985                 990

Pro Gln Trp Ser Leu Gly Pro Trp  Ser Gln Cys Ser Lys  Thr Cys Gly
        995                 1000                1005

Arg Gly  Val Arg Lys Arg Glu  Leu Leu Cys Lys Gly  Ser Ala Ala
    1010                1015                1020

Glu Thr  Leu Pro Glu Ser Gln  Cys Thr Ser Leu Pro  Arg Pro Glu
    1025                1030                1035

Leu Gln  Glu Gly Cys Val Leu  Gly Arg Cys Pro Lys  Asn Ser Arg
    1040                1045                1050

Leu Gln  Trp Val Ala Ser Ser  Trp Ser Glu Cys Ser  Ala Thr Cys
    1055                1060                1065

Gly Leu  Gly Val Arg Lys Arg  Glu Met Lys Cys Ser  Glu Lys Gly
    1070                1075                1080

Phe Gln  Gly Lys Leu Ile Thr  Phe Pro Glu Arg Arg  Cys Arg Asn
    1085                1090                1095

Ile Lys  Lys Pro Asn Leu Asp  Leu Glu Glu Thr Cys  Asn Arg Arg
    1100                1105                1110

Ala Cys  Pro Ala His Pro Val  Tyr Asn Met Val Ala  Gly Trp Tyr
    1115                1120                1125

Ser Leu  Pro Trp Gln Gln Cys  Thr Val Thr Cys Gly  Gly Gly Val
    1130                1135                1140

Gln Thr  Arg Ser Val His Cys  Val Gln Gln Gly Arg  Pro Ser Ser
    1145                1150                1155

Ser Cys  Leu Leu His Gln Lys  Pro Pro Val Leu Arg  Ala Cys Asn
    1160                1165                1170

Thr Asn  Phe Cys Pro Ala Pro  Glu Lys Arg Glu Asp  Pro Ser Cys
    1175                1180                1185

Val Asp  Phe Phe Asn Trp Cys  His Leu Val Pro Gln  His Gly Val
    1190                1195                1200

Cys Asn  His Lys Phe Tyr Gly  Lys Gln Cys Cys Lys  Ser Cys Thr
    1205                1210                1215

Arg Lys  Ile
    1220
```

<210> SEQ ID NO 12
<211> LENGTH: 340
<212> TYPE: PRT
<213> ORGANISM: Homo sapiens

<400> SEQUENCE: 12

```
Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ser Ile Thr Ser Thr Gly Met Glu Thr Arg Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Gly Lys Ser His Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Thr Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Thr Ala Ser Phe Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Arg Lys Ser Tyr Pro Arg Thr Phe Gly Gln Gly Thr Lys Val Glu Ile
225                 230                 235                 240

Lys Arg Gly Ser Thr Ser Gly Gly Ser Thr Ser Gly Gly Ser Thr Ser
                245                 250                 255

Gly Ser Gly Ser Gly Ile Cys Lys Thr Gly Asn Gly Lys Asn Tyr Arg
            260                 265                 270

Gly Thr Met Ser Lys Thr Lys Asn Gly Ile Thr Cys Gln Lys Trp Ser
        275                 280                 285

Ser Thr Ser Pro His Arg Pro Arg Phe Ser Pro Ala Thr His Pro Ser
    290                 295                 300

Glu Gly Leu Glu Glu Asn Tyr Cys Arg Asn Pro Asp Asn Asp Pro Gln
305                 310                 315                 320

Gly Pro Trp Cys Tyr Thr Thr Asp Pro Glu Lys Arg Tyr Asp Tyr Cys
                325                 330                 335

Asp Ile Leu Glu
            340
```

<210> SEQ ID NO 13
<211> LENGTH: 242
<212> TYPE: PRT
<213> ORGANISM: Homo sapiens

<400> SEQUENCE: 13

```
Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30
```

```
Ser Tyr Ala Met Ser Trp Val Arg Gln Ala Pro Gly Lys Gly Leu Glu
        35                  40                  45

Trp Val Ser Ser Ile Thr Ser Thr Gly Met Glu Thr Arg Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Gly Lys Ser His Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Thr Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Thr Ala Ser Phe Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Arg Lys Ser Tyr Pro Arg Thr Phe Gly Gln Gly Thr Lys Val Glu Ile
225                 230                 235                 240

Lys Arg


<210> SEQ ID NO 14
<211> LENGTH: 127
<212> TYPE: PRT
<213> ORGANISM: Mus musculus

<400> SEQUENCE: 14

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Leu Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asn Asp Thr Gly Ile Tyr Tyr Cys Ala
                85                  90                  95

Arg Arg Ser Pro Ser Tyr Tyr Arg Tyr Asp Gly Ala Gly Pro Tyr Tyr
            100                 105                 110

Ala Met Asp Tyr Trp Gly Gln Gly Thr Ser Val Thr Val Ser Ser
        115                 120                 125


<210> SEQ ID NO 15
<211> LENGTH: 112
<212> TYPE: PRT
<213> ORGANISM: Mus musculus
```

<400> SEQUENCE: 15

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Ser His Val Pro Tyr Thr Phe Gly Gly Gly Thr Lys Leu Glu Ile Lys
            100                 105                 110
```

<210> SEQ ID NO 16
<211> LENGTH: 20
<212> TYPE: PRT
<213> ORGANISM: Artificial
<220> FEATURE:
<223> OTHER INFORMATION: linker

<400> SEQUENCE: 16

```
Gly Ser Thr Ser Gly Gly Ser Thr Ser Gly Gly Ser Thr Ser Gly Ser
1               5                   10                  15

Gly Ser Gly Ile
            20
```

<210> SEQ ID NO 17
<211> LENGTH: 18
<212> TYPE: PRT
<213> ORGANISM: Homo sapiens

<400> SEQUENCE: 17

```
Val Gln Thr Arg Ser Val His Cys Val Gln Gln Gly Arg Pro Ser Ser
1               5                   10                  15

Ser Cys
```

<210> SEQ ID NO 18
<211> LENGTH: 18
<212> TYPE: PRT
<213> ORGANISM: Artificial
<220> FEATURE:
<223> OTHER INFORMATION: ADAMTS-18 scrambled peptide

<400> SEQUENCE: 18

```
Val Gln Thr Arg Ser Val Gln Val His Cys Gln Gly Arg Pro Ser Ser
1               5                   10                  15

Ser Cys
```

<210> SEQ ID NO 19
<211> LENGTH: 18
<212> TYPE: PRT
<213> ORGANISM: Homo sapiens

<400> SEQUENCE: 19

```
Cys Ala Pro Glu Ser Ile Glu Phe Pro Val Ser Glu Ala Arg Val Leu
1               5                   10                  15

Glu Asp
```

<210> SEQ ID NO 20
<211> LENGTH: 188
<212> TYPE: PRT
<213> ORGANISM: Homo sapiens

<400> SEQUENCE: 20

```
Leu Pro Arg Pro Glu Leu Gln Glu Gly Cys Val Leu Gly Arg Cys Pro
1               5                   10                  15

Lys Asn Ser Arg Leu Gln Trp Val Ala Ser Ser Trp Ser Glu Cys Ser
            20                  25                  30

Ala Thr Cys Gly Leu Gly Val Arg Lys Arg Glu Met Lys Cys Ser Glu
        35                  40                  45

Lys Gly Phe Gln Gly Lys Leu Ile Thr Phe Pro Glu Arg Arg Cys Arg
    50                  55                  60

Asn Ile Lys Lys Pro Asn Leu Asp Leu Glu Glu Thr Cys Asn Arg Arg
65                  70                  75                  80

Ala Cys Pro Ala His Pro Val Tyr Asn Met Val Ala Gly Trp Tyr Ser
                85                  90                  95

Leu Pro Trp Gln Gln Cys Thr Val Thr Cys Gly Gly Gly Val Gln Thr
            100                 105                 110

Arg Ser Val His Cys Val Gln Gln Gly Arg Pro Ser Ser Ser Cys Leu
        115                 120                 125

Leu His Gln Lys Pro Pro Val Leu Arg Ala Cys Asn Thr Asn Phe Cys
    130                 135                 140

Pro Ala Pro Glu Lys Arg Glu Asp Pro Ser Cys Val Asp Phe Phe Asn
145                 150                 155                 160

Trp Cys His Leu Val Pro Gln His Gly Val Cys Asn His Lys Phe Tyr
                165                 170                 175

Gly Lys Gln Cys Cys Lys Ser Cys Thr Arg Lys Ile
            180                 185
```

<210> SEQ ID NO 21
<211> LENGTH: 66
<212> TYPE: PRT
<213> ORGANISM: Homo sapiens

<400> SEQUENCE: 21

```
Pro Ser Ser Ser Cys Leu Leu His Gln Lys Pro Pro Val Leu Arg Ala
1               5                   10                  15

Cys Asn Thr Asn Phe Cys Pro Ala Pro Glu Lys Arg Glu Asp Pro Ser
            20                  25                  30

Cys Val Asp Phe Phe Asn Trp Cys His Leu Val Pro Gln His Gly Val
        35                  40                  45

Cys Asn His Lys Phe Tyr Gly Lys Gln Cys Cys Lys Ser Cys Thr Arg
    50                  55                  60

Lys Ile
65
```

<210> SEQ ID NO 22
<211> LENGTH: 384
<212> TYPE: PRT
<213> ORGANISM: Artificial
<220> FEATURE:
<223> OTHER INFORMATION: ADAMTS-18 scrambled first fragment

<400> SEQUENCE: 22

```
Asn Glu Thr Leu Val Phe Glu Ile Leu Met Gln Gly Lys Asn Pro Gly
1               5                   10                  15
```

```
Ile Ala Trp Lys Tyr Ala Leu Pro Lys Val Met Asn Gly Thr Pro Pro
            20                  25                  30

Ala Thr Lys Arg Pro Ala Tyr Thr Trp Ser Ile Val Gln Ser Glu Cys
        35                  40                  45

Ser Val Ser Cys Gly Gly Gly Tyr Ile Asn Val Lys Ala Ile Cys Leu
    50                  55                  60

Arg Asp Gln Asn Thr Gln Val Asn Ser Ser Phe Cys Ser Ala Lys Thr
65                  70                  75                  80

Lys Pro Val Thr Glu Pro Lys Ile Cys Asn Ala Phe Ser Cys Pro Ala
                85                  90                  95

Tyr Trp Met Pro Gly Glu Trp Ser Thr Cys Ser Lys Ala Cys Ala Gly
            100                 105                 110

Gly Gln Gln Ser Arg Lys Ile Gln Cys Val Gln Lys Lys Pro Phe Gln
        115                 120                 125

Lys Glu Glu Ala Val Leu His Ser Leu Cys Pro Val Ser Thr Pro Thr
    130                 135                 140

Gln Val Gln Ala Cys Asn Ser His Ala Cys Pro Pro Gln Trp Ser Leu
145                 150                 155                 160

Gly Pro Trp Ser Gln Cys Ser Lys Thr Cys Gly Arg Gly Val Arg Lys
                165                 170                 175

Arg Glu Leu Leu Cys Lys Gly Ser Ala Ala Glu Thr Leu Pro Glu Ser
            180                 185                 190

Gln Cys Thr Ser Leu Pro Arg Pro Glu Leu Gln Glu Gly Cys Val Leu
        195                 200                 205

Gly Arg Cys Pro Lys Asn Ser Arg Leu Gln Trp Val Ala Ser Ser Trp
    210                 215                 220

Ser Glu Cys Ser Ala Thr Cys Gly Leu Gly Val Arg Lys Arg Glu Met
225                 230                 235                 240

Lys Cys Ser Glu Lys Gly Phe Gln Gly Lys Leu Ile Thr Phe Pro Glu
                245                 250                 255

Arg Arg Cys Arg Asn Ile Lys Lys Pro Asn Leu Asp Leu Glu Glu Thr
            260                 265                 270

Cys Asn Arg Arg Ala Cys Pro Ala His Pro Val Tyr Asn Met Val Ala
        275                 280                 285

Gly Trp Tyr Ser Leu Pro Trp Gln Gln Cys Thr Val Thr Cys Gly Gly
    290                 295                 300

Gly Val Gln Thr Arg Ser Val Gln Val His Cys Gln Gly Arg Pro Ser
305                 310                 315                 320

Ser Ser Cys Leu Leu His Gln Lys Pro Pro Val Leu Arg Ala Cys Asn
                325                 330                 335

Thr Asn Phe Cys Pro Ala Pro Glu Lys Arg Glu Asp Pro Ser Cys Val
            340                 345                 350

Asp Phe Phe Asn Trp Cys His Leu Val Pro Gln His Gly Val Cys Asn
        355                 360                 365

His Lys Phe Tyr Gly Lys Gln Cys Cys Lys Ser Cys Thr Arg Lys Ile
    370                 375                 380
```

```
<210> SEQ ID NO 23
<211> LENGTH: 20
<212> TYPE: DNA
<213> ORGANISM: Artificial
<220> FEATURE:
<223> OTHER INFORMATION: sense primer

<400> SEQUENCE: 23

ccatggccga ggtgcagctg                                                20
```

<210> SEQ ID NO 24
<211> LENGTH: 20
<212> TYPE: DNA
<213> ORGANISM: Artificial
<220> FEATURE:
<223> OTHER INFORMATION: antisense primer

<400> SEQUENCE: 24
cgggccgcac tctttggtcc 20

<210> SEQ ID NO 25
<211> LENGTH: 31
<212> TYPE: DNA
<213> ORGANISM: Artificial
<220> FEATURE:
<223> OTHER INFORMATION: sense primer

<400> SEQUENCE: 25
agctcatatg tgcaagactg ggaatggaaa g 31

<210> SEQ ID NO 26
<211> LENGTH: 31
<212> TYPE: DNA
<213> ORGANISM: Artificial
<220> FEATURE:
<223> OTHER INFORMATION: antisense primer

<400> SEQUENCE: 26
tcctctcgag ctcaagaatg tcgcagtagt c 31

<210> SEQ ID NO 27
<211> LENGTH: 30
<212> TYPE: DNA
<213> ORGANISM: Artificial
<220> FEATURE:
<223> OTHER INFORMATION: SCFN primer

<400> SEQUENCE: 27
ggaattccat atggccgagg tgcagctgtt 30

<210> SEQ ID NO 28
<211> LENGTH: 65
<212> TYPE: DNA
<213> ORGANISM: Artificial
<220> FEATURE:
<223> OTHER INFORMATION: SCFC primer

<400> SEQUENCE: 28
actagtagat ccaccacttg tcgacccacc agaagtactt ccccgtttga tttccacctt 60
ggtcc 65

<210> SEQ ID NO 29
<211> LENGTH: 59
<212> TYPE: DNA
<213> ORGANISM: Artificial
<220> FEATURE:
<223> OTHER INFORMATION: forward primer KRN

<400> SEQUENCE: 29
caagtggtgg atctactagt ggctctggat ccggaatttg caagactggg aatggaaag 59

<210> SEQ ID NO 30
<211> LENGTH: 36
<212> TYPE: DNA
<213> ORGANISM: Artificial

<220> FEATURE:
<223> OTHER INFORMATION: backward primer KRC

<400> SEQUENCE: 30
taggatccgc ggccgcctca agaatgtcgc agtagt 36

<210> SEQ ID NO 31
<211> LENGTH: 7
<212> TYPE: PRT
<213> ORGANISM: Artificial
<220> FEATURE:
<223> OTHER INFORMATION: clone

<400> SEQUENCE: 31

```
Val His Cys Val Gln Leu Tyr
1               5
```

<210> SEQ ID NO 32
<211> LENGTH: 516
<212> TYPE: PRT
<213> ORGANISM: Artificial
<220> FEATURE:
<223> OTHER INFORMATION: PAC-1 bifunctional agent

<400> SEQUENCE: 32

```
Met Ala Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ser Ile Thr Ser Thr Gly Met Glu Thr Arg Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Gly Lys Ser His Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Thr Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Ile Ser Ser Tyr Leu Asn Trp Tyr Gln Gln Lys Pro Gly Lys
                165                 170                 175

Ala Pro Lys Leu Leu Ile Tyr Thr Ala Ser Phe Leu Gln Ser Gly Val
            180                 185                 190

Pro Ser Arg Phe Ser Gly Ser Gly Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Arg Lys Ser Tyr Pro Arg Thr Phe Gly Gln Gly Thr Lys Val Glu Ile
225                 230                 235                 240

Lys Arg Gly Ser Thr Ser Gly Gly Ser Thr Ser Gly Gly Ser Thr Ser
                245                 250                 255

Gly Ser Gly Ser Gly Ile Gln Val Gln Leu Lys Gln Ser Gly Pro Gly
            260                 265                 270
```

-continued

```
Leu Val Gln Pro Ser Gln Ser Leu Ser Ile Thr Cys Thr Val Ser Gly
        275                 280                 285

Phe Ser Leu Thr Ser Tyr Gly Val His Trp Val Arg Leu Ser Pro Gly
    290                 295                 300

Lys Gly Leu Glu Trp Leu Gly Val Ile Trp Ser Gly Gly Ser Thr Asp
305                 310                 315                 320

Tyr Asn Ala Ala Phe Ile Ser Arg Leu Ser Ile Ser Lys Asp Asn Ser
                325                 330                 335

Lys Ser Gln Val Phe Phe Lys Met Asn Ser Leu Gln Ala Asn Asp Thr
            340                 345                 350

Gly Ile Tyr Tyr Cys Ala Arg Arg Ser Pro Ser Tyr Tyr Arg Tyr Asp
        355                 360                 365

Gly Ala Gly Pro Tyr Tyr Ala Met Asp Tyr Trp Gly Gly Gly Thr Ser
    370                 375                 380

Val Thr Val Ser Ser Gly Gly Gly Gly Ser Gly Gly Gly Gly Ser Gly
385                 390                 395                 400

Gly Gly Gly Ser Asp Val Leu Met Thr Gln Thr Pro Leu Ser Leu Pro
                405                 410                 415

Val Ser Leu Gly Asp Gly Ala Ser Ile Ser Cys Arg Ser Ser Gln Ser
            420                 425                 430

Ile Val His Ser Asn Gly Asn Thr Tyr Leu Glu Trp Tyr Leu Gln Lys
        435                 440                 445

Pro Gly Gly Ser Pro Lys Leu Leu Ile Tyr Lys Val Ser Asn Arg Phe
    450                 455                 460

Ser Gly Val Pro Asp Arg Phe Thr Gly Ser Gly Ser Gly Thr Asp Phe
465                 470                 475                 480

Thr Leu Lys Ile Ser Arg Val Glu Ala Glu Asp Leu Gly Val Tyr Tyr
                485                 490                 495

Cys Trp Gly Gly Ser His Val Pro Tyr Thr Phe Gly Gly Gly Thr Lys
            500                 505                 510

Leu Glu Ile Lys
        515
```

THERAPEUTIC AGENTS FOR INDUCING PLATELET FRAGMENTATION AND TREATING THROMBOEMBOLIC DISORDERS

This application claims the benefit of U.S. Provisional Patent Application Ser. No. 61/174,620, filed May 1, 2009, which is hereby incorporated by reference in its entirety.

This invention was made with government support under grant number HL13336 and DA004315 awarded by the National Institute of Health. The government has certain rights in this invention.

FIELD OF THE INVENTION

The present invention relates to therapeutic agents for inducing platelet fragmentation and treating thromboembolic disorders.

BACKGROUND OF THE INVENTION

Blood clotting involves a complicated cascade of events to signal the platelets and fibrin to form the clot. Thrombosis is the formation of blood clot (thrombus) inside a blood vessel, obstructing the flow of blood. Embolism occurs when a blood clot, migrates from one part of the body usually through the circulatory system and causes a blockage or occlusion in another part of the body. The occlusion can also occur at the site of thrombus formation without any migration. A thromboembolic disorder refers both to thrombosis and its principal complication which is embolization (migration of thrombus and occlusion).

At the cellular level, thrombus formation is characterized by rapid conformational changes leading to activation of blood platelets and of various plasma proproteins. In response to a range of triggering stimuli and cascading events, zymogenic prothrombin is catalyzed to thrombin. In turn, thrombin acts upon the soluble structure protein fibrinogen, cleaving the N-terminal A and B polypeptides from the alpha and beta chains to form fibrin monomer. Cleavage results in redistribution of charge density and exposure of two polymerization sites, enabling growth of the monomer into an insoluble, three dimensional polymeric network. Concurrently, thrombin acts to induce significant physiological change to a "resting" or inactive blood platelet by changing its shape. This is associated with thromboxane $A_2$ synthesis and release of ADP from intraplatelet storage granules which enhances platelet aggregation. Such activated platelets play a dual role in hemostasis:

a) They are more adhesive and capable of binding fibrinogen and von Willebrand factor. Activated platelets adhere to subendothelial von Willebrand factor via the GPIb receptor and co-aggregate with fibrinogen and von Willebrand factor via the GPIIb-IIIa.
b) Activated platelets act as a catalytic surface for thrombin generation from its plasma pro-enzymes. This results in the formation of insoluble fibrin intermeshed within and around the platelet thrombus. This three dimensional platelet plug under pathophysiological conditions can serve to compromise circulatory system patency leading to stroke, tissue infarction, and necrosis.

Thrombus formation can be pathogenic and is a causative factor in ischemic heart disease (myocardial infarction, unstable angina), ischemic stroke, deep vein thrombosis, pulmonary embolism, and related conditions. Vascular disease can result in hypercoagulable states, resulting in thrombus formation. Consequences of ischemic stroke include loss of function of the affected region and death.

Appearance of atherosclerotic plaques within the coronary arteries is the precursor to ischemic heart disease (IHD). Causative factors for ischemic stroke include cardiogenic emboli, atherosclerotic emboli, and penetrating artery disease. Migration of the embolus through the aorta into the carotids can result in closure of a cerebral vessel. Pulmonary embolism results from the migration of the embolus from a formation site within the deep veins of the extremities into the pulmonary vasculature. In the event of an acute blockage, consequences include rapid death by heart failure. Formation of thrombi within the deep veins of the lower extremities is characterized as deep vein thrombosis. Causative factors include blood stasis. Certain surgical procedures also correlate strongly with postoperative venous clot formation.

Stroke, a thromboembolic disorder, is the second largest cause of death in the world. Platelets play a major role in this process as first demonstrated by the beneficial effect of aspirin on stroke development or reoccurrence. There are 2 major forms of occlusive stroke formation: (a) Release of ruptured plaque and fibrin thrombi from a stenosed carotid; (b) atrial fibrillation leading to cardiac thrombus embolization. Both mechanisms are associated with distal vessel post ischemic occlusion (reperfusion injury) secondary to deposition of platelets and fibrin on anoxia-induced activated endothelial cells (Zhang et al., "Dynamic Platelet Accumulation at the Site of the Occluded Middle Cerebral Artery and in Downstream Microvessels is Associated with Loss of Microvascular Integrity After Embolic Middle Cerebral Artery Occlusion," *Brain Res* 912:181-94 (2001); Choudhri et al., "Reduced Microvascular Thrombosis and Improved Outcome in Acute Murine Stroke by Inhibiting GPIIb/IIIa Receptor-mediated Platelet Aggregation," *J Clin Invest* 102:1301-10 (1998); del Zoppo, "The Role of Platelets in Ischemic Stroke," *Neurology* 51:S9-14 (1998)). During high shear forces, platelets adhere weakly to endothelium via conformationally-induced Von Willebrand Factor (VWF) binding to the platelet GPIb-V-IX receptor. This is followed by inside-out intracellular platelet signaling which activates the conformation of the major platelet Integrin receptor, $\alpha IIb\beta 3$ (GPIIb-GPIIIa). This forms a more permanent, stable platelet aggregate (via fibrinogen bridging of GPIIb-IIIa receptor) on adjacent platelets. These activated platelets generate thrombin on their surface which leads to deposition of fibrin fibers within and outside of the thrombus.

Ischemic post-infusion platelet aggregation has been described to occur 1 hr after initial occlusion to as long as 23 hrs after reperfusion, both indirectly by $^{111}$In-labelled platelet deposition (Choudhri et al., "Reduced Microvascular Thrombosis and Improved Outcome in Acute Murine Stroke by Inhibiting GPIIb/IIIa Receptor-mediated Platelet Aggregation," *J Clin Invest* 102:1301-10 (1998)) as well as scanning electron microscopy of cerebral vessels distal to the initial lesion (Zhang et al., "Dynamic Platelet Accumulation at the Site of the Occluded Middle Cerebral Artery and in Downstream Microvessels is Associated with Loss of Microvascular Integrity After Embolic Middle Cerebral Artery Occlusion," *Brain Res* 912:181-94 (2001)).

Therapeutic lysis of pathogenic thrombi (thrombolysis) is achieved by administering thrombolytic agents. Benefits of thrombolytic therapy include rapid lysis of the thromboembolic disorder and restoration of normal circulatory function. Currently, there are mainly three thrombolytic strategies used clinically. First, inhibition of thrombin by either the indirect thrombin inhibitor heparin or direct thrombin inhibitors, such as hirudin (Meyer et al., "Local Delivery of r-Hirudin by a Double-balloon Perfusion Catheter Prevents Mural Thrombosis and Minimizes Platelet Deposition after Angioplasty," *Circulation* 90:2474-2480 (1994); Topol et al., "Recombinant Hirudin for Unstable Angina Pectoris: A Multicenter, Randomized Angiographic Trial," *Circulation* 89:1557-1566 (1994); Cannon et al., "Hirudin: Initial Results in Acute Myocardial Infarction, Unstable Angina and Angioplasty," *J Am Coll Cardiol* 25:30 S-37S (1995)). Second, administration of Integrin αIIbβ3 (platelet glycoprotein GPIIb/IIIa) antagonists such as abciximab, tirofiban, and eptifibatide that affect the attachment of platelet to fibrinogen by mimicking RGD binding site (Tam et al., "Abciximab (ReoPro chimeric 7E3 Fab) Demonstrates Equivalent Affinity and Functional Blockade of Glycoprotein IIb/IIIa and Alpha(V) Beta3 Integrins," *Circulation* 98:1085-1091 (1998); Lefkovits, "Platelet Glycoprotein IIb/IIIa Receptor Antagonists in Coronary Artery Disease," *Eur. Heart. J.* 17:9-18 (1996); Scarborough et al., "Platelet Glycoprotein IIb/IIIa Antagonists: What are the Relevant Issues Concerning their Pharmacology and Clinical Use?"*Circulation* 100:437-444 (1999)). Third, using blood clot-dissolving agents such as TPA, streptokinase, and urokinase to make thrombolytics effective in dissolving fibrin around thrombi (Topol et al., "A Multi-center, Randomized, Placebo-controlled Trial of a New Form of Intravenous Recombinant Tissue-type Plasminogen Activator (Activase) in Acute Myocardial Infarction," *J Am Coll Cardiol* 9:1205-1213 (1987); Marler et al., "Stroke: tPA and the Clinic," *Science* 301:1677 (2003); Collen, "Towards Improved Thrombolytic Therapy," *Lancet* 342: 34-36 (1993)). Although the above treatments have been partially successfully, some of the treated patients suffer from bleeding complications, such as hemorrhagic stroke (Sakharov et al., "Superficial Accumulation of Plasminogen During Plasma Clot Lysis," *Circulation* 92: 1883-1890 (1995)). Complications include internal and external bleeding due to lysis of physiologic clots, and stroke resulting in cerebral hemorrhage.

For example, TPA is associated with secondary toxicity, such as hypofibrinogenemia and bleeding. Also, successful application of thrombolytics in ischemic stroke has not been realized. Current treatment of occlusive stroke with TPA, an agent which must be given within 3 hrs of occlusion (Su et al., "Activation of PDGF-CC by Tissue Plasminogen Activator Impairs Blood-brain Barrier Integrity During Ischemic Stroke," *Nat Med* 14:731-737 (2008); Choi et al., "Endovascular Recanalization Therapy in Acute Ischemic Stroke," *Stroke* 37:419-24 (2006)), is operationally feasible in ~10% of stroke patients. A later infusion runs the risk of cerebral hemorrhage.

Animal stroke experiments with anti-platelet GPIIb-IIIa agents have successfully diminished brain infarct formation as well as permanent neurological damage (Choudhri et al., "Reduced Microvascular Thrombosis and Improved Outcome in Acute Murine Stroke by Inhibiting GPIIb/IIIa Receptor-mediated Platelet Aggregation," *J Clin Invest* 102:1301-10 (1998); Abumiya et al., "Integrin α(IIb)β(3) Inhibitor Preserves Microvascular Patency in Experimental Acute Focal Cerebral Ischemia," *Stroke* 31:1402-09 (2000)). However, this has been associated with increased cerebral hemorrhage and death, since antibodies against GPIIb-IIIa inhibit platelet function and induce thrombocytopenia. The development of a different approach to inhibit arterial bleeding and associated thromboembolic disorders by lysis of platelet thrombus with specific anti-GPIIIa(49-66) antibodies would be of significant clinical value. A recent clinical study on the role of Abciximab (anti-GPIIB-IIIa) in stroke was discontinued because of its high rate of hemorrhage as well as ineffectiveness (Adams et al., "Emergency Administration of Abciximab for Treatment of Patients with Acute Ischemic Stroke: Results of an International Phase III Trial: Abciximab in Emergency Treatment of Stroke Trial (AbESTT-II)," *Stroke* 39:87-99 (2008)).

The present invention is directed to overcoming these and other deficiencies in the art.

SUMMARY OF THE INVENTION

One aspect of the present invention is directed to a therapeutic agent. The therapeutic agent comprises a GPIIIa(49-66)-specific targeting agent and a thrombi-specific homing agent linked to the GPIIIa(49-66)-specific targeting agent.

Another aspect of the present invention is directed to a method of treating thromboembolic disorders in a subject. This method involves administering the therapeutic agent to the subject under conditions effective to treat thromboembolic disorders in the subject.

Another aspect of the present invention is directed to a method of inducing platelet fragmentation in a subject. This method involves administering the therapeutic agent to a subject under conditions effective to induce platelet thrombi fragmentation in the subject.

The therapeutic agent of the present invention is unique in that it has no effect on platelet function and minimal effect on platelet count (<15% decrease). These agents dissolve already-formed platelet thrombi by binding to activated platelets within the platelet thrombus as well as to activated early platelet deposition on post ischemic endothelial cells. This therapeutic agent is, therefore, safer as well as more efficient than conventional anti-GPIIIa antibodies which block platelet function and induce thrombocytopenia and mortality, due to GPIIb-IIIa activation (Quinn et al., "Platelet Glycoprotein IIb/IIIa Inhibitors: Recognition of a Two-Edged Sword?," *Circulation* 106:379-85 (2002); Cox, "Oral GPIIb/IIIa Antagonists: What Went Wrong?" *Curr Pharm Des* 10:1587-96 (2004); Hanson et al., "Progress in the Field of GPIIb/IIIa Antagonists," *Curr Med Chem Cardiovasc Hematol Agents* 2:157-67 (2004); Bassler et al., "A Mechanistic Model for Paradoxical Platelet Activation by Ligand-Mimetic AlphaIIbBeta3 (GPIIb/IIIa) Antagonists," *Arterioscler Thromb Vasc Biol* 27:e9-15 (2007); Su et al., "Activation of PDGF-CC by Tissue Plasminogen Activator Impairs Blood-Brain Barrier Integrity During Ischemic Stroke," *Nat Med* 14:731-7 (2008), which are hereby incorporated by reference in their entirety). In addition, the therapeutic agent of the present invention includes human antibodies without an Fc domain. As a result, they do not activate complement.

BRIEF DESCRIPTION OF THE DRAWINGS

FIG. 1A shows an ELISA in which scFv library I and J clones from each round of panning against GPIIIa(49-66) peptide were coated on a Microtiter 96-well microplate (n=3). FIG. 1B shows an ELISA after three rounds of panning Individual clones from library J were measured for their ability to bind to GPIIIa(49-66) peptide coated on the microplate. The concentration of phage antibodies was normalized and the dilutions (black and gray columns) were 1:3 and 1:9 in PBS, respectively (n=3).

FIG. 2A shows the construction and expression scFv-A11. "M" is a protein marker; lane 1 is total bacteria proteins from uninduced cells; lane 2 and 3 are total bacteria proteins after 1 h and 4 h, respectively, of induction with 1 mM IPTG. FIG. 2B shows the 12% SDS-PAGE analysis of the purity of refolded scFv-A11 over a Ni-NTA column. "M" is a protein marker; Lane 1-4 are the fractions collected from the Ni-NTA column.

FIGS. 3A-B shows the sequence for the scFv-A11 clone. FIG. 3A shows the nucleic acid sequences of $V_H$ DNA (SEQ ID NO: 1), $V_L$ DNA (SEQ ID NO: 2) and the linker (SEQ ID NO: 3). FIG. 3B shows the deduced amino acid sequence for $V_H$ (SEQ ID NO: 4), $V_L$ (SEQ ID NO: 5), and the linker (SEQ ID NO: 6) of the scFv-A11 clone. The human monoclonal antibody scFv-A11 has an IgG1 isotype, and the light chains are κ chains. The scFv gene is 242 amino acids total: the $V_H$ domain is 118 amino acids; the linker sequence, $(Gly_4Ser)_3$, is 15 amino acids; the $V_L$ domain is 109 amino acids.

FIG. 5A shows the data on effect of the control (Ctl) (scrambled [sc] ADAMTS-18F or inactive ADAMTS-18 66 aa fragment), PtIgG (Patient anti-GPIIIa(49-66)), media, and AD-18F on collagen induced platelet aggregates incubated for 0.5, 1, 2, 4, and 8 hrs at 37° C. The data shows the number of platelets/aggregate vs time. Note that both AD-18F and anti-GPIIIa(49-66) have a similar kinetic effect, representative of 3 collagen aggregate experiments. FIG. 5B shows photomicrographs of platelet collagen aggregates before and after treatment with anti-GPIIIa(49-66) or AD-18F or control ((inactive) 66 aa ADAMTS-18 fragment or AD-18F). FIG. 5C shows the effect of prestimulated platelet thrombin receptor, PAR-1 on induction of platelet fragmentation with AD-18F. Gel-filtered platelets were treated with the PAR-1 agonist TFLLRN (SEQ ID NO: 7) (200 μM) for 30 min at 37° C., washed, and then followed with varying AD-18F concentrations (50-6 μg/ml) for 4 hrs. Gray and black bars are, respectively, without and with TFLLRN (SEQ ID NO: 7) prestimulation. There is increased sensitivity of activated platelets to AD-18F at low AD-18F concentration. FIG. 5D shows the effect of anti-ADAMTS-18 antibody on mouse tail bleeding time. BALB/c mice were injected i.v. with 50 μg of anti-ADAMTS-18 IgG (AD-IgG) or preimmune sera IgG (PIS-IgG) and their bleeding time monitored 60 min later, n=10. There is a 4.5-fold decrease in bleeding time with Ab-IgG, p=0.002.

FIGS. 6A and 6B show the effect of AD-18F on carotid artery occlusion. Swiss-Webster mice were injected i.v. with 25 μg of AD-18F or control (scrambled (sc AD-18F) or inactive 66 aa AD-189), or AD-18F. The right carotid artery was exposed and an $FeCl_3$ filter paper patch applied 2 hr after i.v. injection. Blood flow (ml/min) was measured with a Doppler flow apparatus. FIG. 6A shows the mean continuous flow measured in 6 control (inactive 66 aa fragment) and 6 experimental (AD-18F) mice over a period of 38-43 min. FIG. 6B shows the same experiment plotted every 5 min as well as a single saline control experiment (SAL). * depicts statistically significant differences (p<0.05) by Student t test, n=5-6, SEM is given. FIGS. 6C and D shows experimental data for scFv-A11. Experimental details are the same as FIGS. 6A and B, except for the use of scFv-A11 or control irrelevant monoclonal IgG (ctl) at 25 μg/ml.

FIG. 8A shows the flow cytometry assay data for gel-filtered human platelets incubated with patient anti-GPIIIa(49-66) Ab (PtIgG), Control IgG (Ctrl), 13CG2 (irrelevant scFv-Ab), and active scFv-A11. FIG. 8B shows the effect of active scFv-A11 on platelet count in vivo.

FIGS. 9A-B show platelet fragmentation induced by human scFv monoclonal anti-GPIIIa(49-66) antibodies selected from phage display library. FIG. 9A shows in vitro platelet fragmentation induced by individual scFv antibody clones as measured by flow cytometry assay. Ctl is control, PtIgG is patient IgG. The various clones are diluted at levels of 1:2 and 1:4 and 1:8, which correspond to the gray, black and white bars, respectively. The data represents the summary of three independent experimental results (n=3). FIG. 9B shows in vitro data for platelet aggregates destroyed by scFv antibody clones (n=3). Serial dilutions of clones 11, 43, 54, and CG2 were made with PBS. For inhibition assays, serial dilutions of clones 11 and 54 were mixed with fixed amounts of clone 43 or CG2 to make the ratio between 11 or 54 with 43 or CG2 as 1:1, 1:2, 1:4, and 1:8 (n=2).

FIG. 10A shows the comparison of saline vehicle (V) vs. i.v. injection of 20 μg of scFv-A11 Ab (A11) or 13CG2 (C) 2 hrs after obstruction and release of right middle cerebral artery. The standard of error of the mean (SEM) is given. FIG. 10B shows post reflex—higher number reflects greater neurologic impairment. *P, student t test (2 tails). FIG. 10C shows a representative TTC stained sections from the three groups.

FIG. 11A shows the schematic diagram describing the cloning strategy. FIG. 11B shows the plasmid construct. FIG. 11C shows a 12% SDS-PAGE analysis of purified fusion protein (~40 kD) with Ni-column induction by 1 mM IPTG.

FIG. 12A shows the binding activity of the scFv-A11 and bifunctional fusion antibody (SLK) on platelet. FIG. 12B shows the induction of platelet fragmentation by scFv-A11 and bifunctional fusion antibody (SLK). FIG. 12C shows the binding activity of scFv-A11 and bifunctional fusion antibody (SLK) on partially digested fibrin.

FIG. 14A shows platelet fragmentation with 18-mer peptide. Gel-filtered platelets were treated with Biotin-peptide (bp) as well as bp+streptavidin (str) and scrambled Biotinylated ADAMTS-18 peptide (scp) to induce integrin clustering, n=6. Platelet fragmentation was assessed by FACS as described in in the examples section. FIG. 14B shows platelet oxidation. CT (control IgG), Ab (patient IgG). 18-mer biotin-peptide was incubated with an anti-Biotin Ab, 1:200 dilution (gray bars) or irrelevant IgG white bars, n=6. Oxidation was assessed. FIG. 14C shows ADAMTS-18 or control protein that was synthesized by ribosomal translation, employing $^{35}$S methionine. $^{35}$S-ADAMTS-18 (131 mCi/mg) was added to gel filtered platelets over night at 4° C., employing doubling concentrations. Ctl refers to $^{35}$S ribosomal-translation of luciferase. AD-CTD refers to $^{35}$S-ribosomal translation of ADAMTS-18 with absent C-terminal 157 amino acids (13% deleted). There is an absence of binding with C-terminal deficient ADAMTS-18. 18 mer refers to 10 μM non-radioactive 18 mer peptide added with the $^{35}$S-ADAMTS-18 incubation. Binding with C-terminal 18 mer peptide is inhibited. The amino acid sequence for the 18-mer peptide is (SEQ ID NO: 8):

1 VQTRSVHCVQ QGRPSSSC

Figure 15:
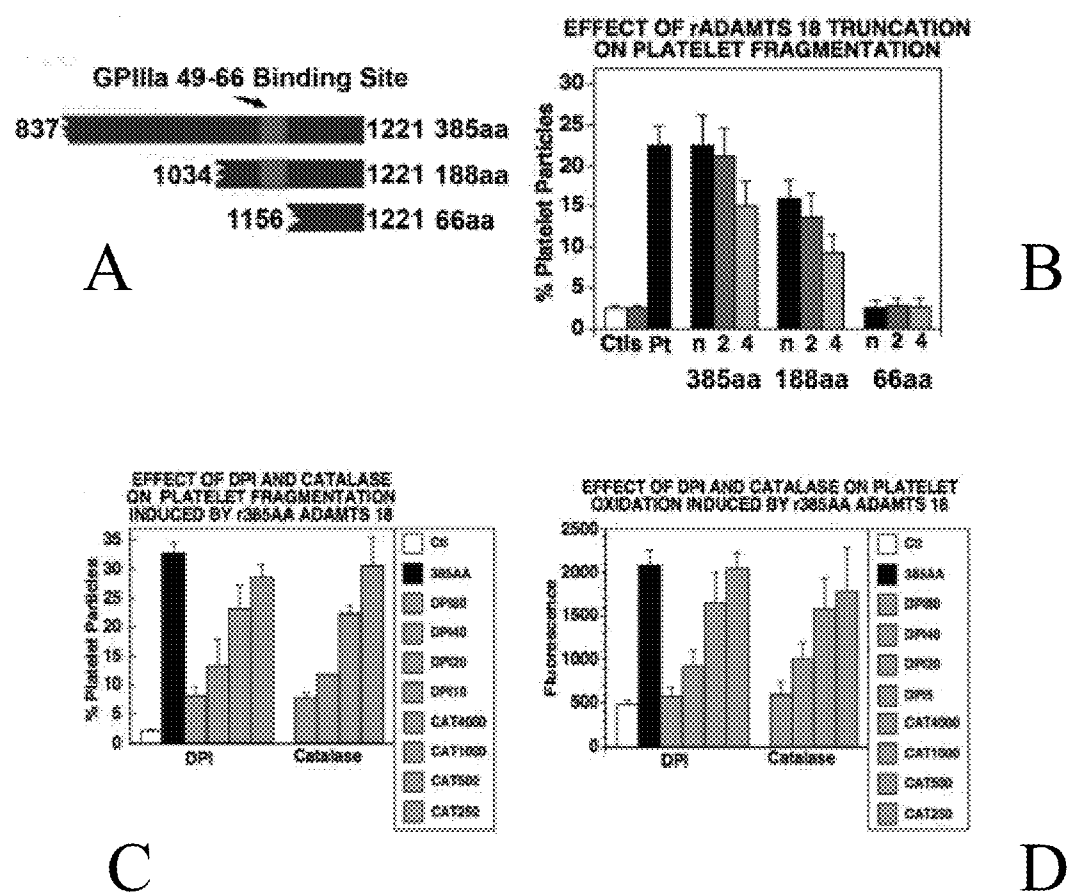

FIGS. 15A-D show the effects of ADAMTS-18 on platelet fragmentation. FIG. 15A depicts a cartoon of truncated ADAMTS-18 constructs. The GPIIIa(49-66) binding site is depicted. Three C-terminal recombinant peptide fragments were tested for their ability to induce platelet fragmentation and oxidation. These included the larger fragment of 385 amino acids (aa) from the C-terminal end, an intermediate fragment of 188 aa, and a smaller fragment of 66 aa. FIG. 15B shows the effect of truncation on platelet fragmentation. Ctls refer to buffer and control IgG. Pt is patient IgG. Dilutions of the 3 fragments—recombinant peptides were made at neat (n), 1:2, and 1:4 in buffer. The initial concentration of the large 385 aa fragment was 1.3 μM, whereas the initial concentration of the 188 aa and 66 aa peptides were 19 and 85 μM, respectively, n=6. FIG. 15C shows that fragmentation induced by the 385 aa fragment is inhibited by DPI (nM) and catalase (units/ml). Ctl refers to control buffer; 385 aa fragment refers to the 1.3 μM 385 aa fragment. DPI 180, 140, 120, and 10 refer to nM DPI+385 aa fragment. CAT 4000, 1000, and 500 refer to catalase units plus 385 aa fragment. Gray bars within the figure vary from left to right, DPI 180-DPI 10; and catalase 4000-250. FIG. 15D shows oxidation induced by 385 aa fragment inhibited by DPI and catalase. The designation in FIG. 15D is the same as in FIG. 15C.

Figure 16:
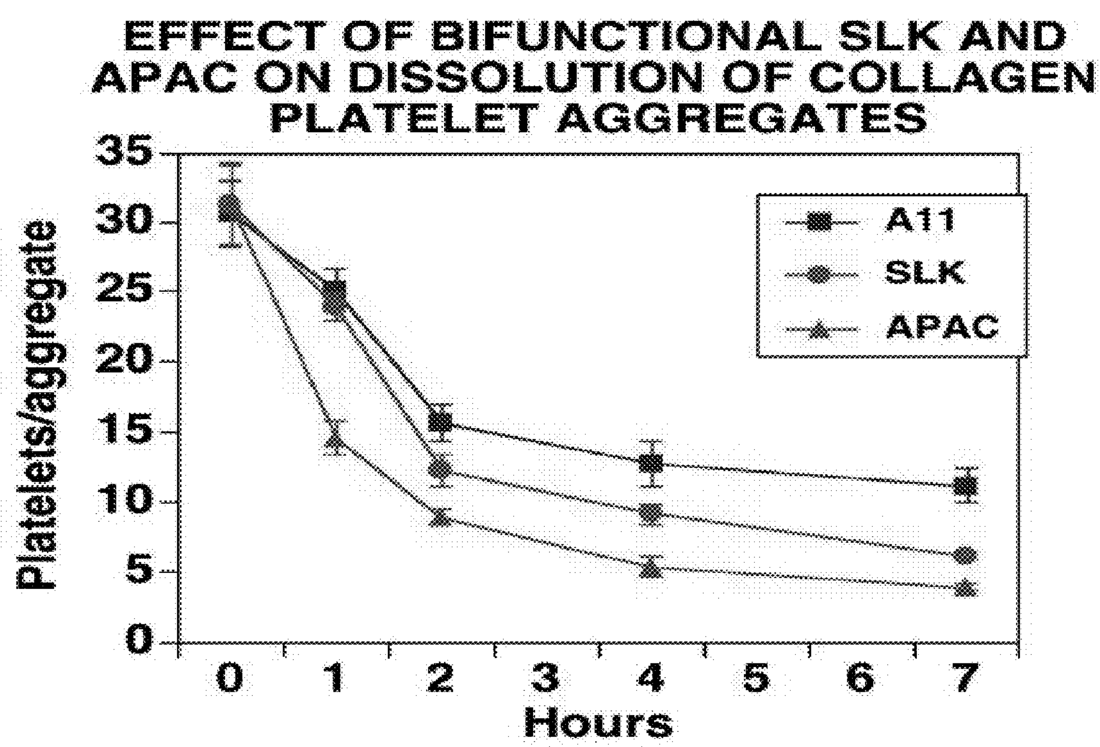

FIG. 16 shows dissolution of ex vivo collagen-induced platelet aggregates with single chain A11 or bifunctional SLK and APAC compounds. Platelet aggregates were prepared by incubating gel-filtered platelets with 1 μg/ml collagen and 100 mg/ml fibrinogen at 37° C. for 1 hr in Tyrode buffer with intermittent shaking The suspension was then allowed to settle at gravity sedimentation for 30 minutes at room temperature. The top 50% volume was discarded and the remainder of the platelet aggregate suspension added directly to Tyrode buffer with 0.85 μM testing agents for enumeration at various time intervals. Data and SEM are given for 3 separate experiments in which each time point represents 5 measurements.

DETAILED DESCRIPTION OF THE INVENTION

One aspect of the present invention is directed to a therapeutic agent. The therapeutic agent comprises a GPIIIa(49-66)-specific targeting agent and a thrombi-specific homing agent linked to the GPIIIa(49-66)-specific targeting agent.

GPIIIa(49-66) is a protein with the amino acid sequence of CAPESIEFPVSEARVLED (SEQ ID NO: 9). This is an epitope of Integrin subunit β3 (GPIIIa) which is expressed on the surface of platelets (Morris et al., "Autoimmune Thrombocytopenic Purpura in Homosexual Men," *Ann Intern Med* 96:714-717 (1982); Najean et al., "The Mechanism of Thrombocytopenia in Patients with HIV Infection," *J Lab Clin Med* 123(3):415-20 (1994), which are hereby incorporated by reference in their entirety).

In one embodiment, the GPIIIa(49-66)-specific targeting agent is an isolated anti-platelet integrin GPIIIa(49-66) antibody. This antibody induces complement-independent platelet oxidative fragmentation and death by generation of platelet peroxide following NADPH oxidase activation. GPIIIa (49-66)-specific antibodies exhibit one or more desirable properties, such as high affinity binding for GPIIIa(49-66), the ability to induce complement-independent platelet oxidative fragmentation and platelet death.

In a preferred embodiment, the GPIIIa(49-66) targeting agent is a single chain monoclonal antibody ("scFv") possessing properties described above. Single chain human (scFv) monoclonal antibodies against GPIIIa(49-66) which induce platelet fragmentation (Li et al., "Platelet Fragmentation Requires a Specific Structural Conformation of Human Monoclonal Antibody against beta3 Integrin," *J Biol Chem* 2008; 283:3224-30 (2008), which is hereby incorporated by reference in its entirety) have been identified using phage display. These monoclonal scFv antibodies are also capable of destroying platelet aggregates. Often, in order to clinically to use antibody induced binding and oxidative platelet fragmentation, a monoclonal antibody is required, because some polyclonal antibodies have cross-reactivity with other antigens. Due to the homology of sequences shared with human GPIIIa(49-66), mouse thrombocytopenia can result. A phage surface display antibody technology system can be successfully used to screen single chain antibodies against GPIIIa (49-66).

In another embodiment, the GPIIIa(49-66)-specific targeting agent is an endogenous C-terminal 385 amino acid fragment of ADAMTS-18 protein (AD-18F) with the following amino acid sequence (SEQ ID NO: 10):

```
  1 NETLVFEILM QGKNPGIAWK YALPKVMNGT PPATKRPAYT WSIVQSECSV SCGGGYINVK
 61 AICLRDQNTQ VNSSFCSAKT KPVTEPKICN AFSCPAYWMP GEWSTCSKAC AGGQQSRKIQ
121 CVQKKPFQKE EAVLHSLCPV STPTQVQACN SHACPPQWSL GPWSQCSKTC GRGVRKRELL
181 CKGSAAETLP ESQCTSLPRP ELQEGCVLGR CPKNSRLQWV ASSWSECSAT CGLGVRKREM
241 KCSEKGFQGK LITFPERRCR NIKKPNLDLE ETCNRRACPA HPVYNMVAGW YSLPWQQCTV
301 TCGGGVQTRS VHCVQQGRPS SSCLLHQKPP VLRACNTNFC PAPEKREDPS CVDFFNWCHL
361 VPQHGVCNHK FYGKQCCKSC TRKI
```

ADAMTS-18 protein has the following amino acid sequence (SEQ ID NO: 11):

```
   1 MECALLLACA FPAAGSGPPR GLAGLGRVAK ALQLCCLCCA SVAAALASDS SSGASGLNDD

  61 YVFVTPVEVD SAGSYISHDI LHNGRKKRSA QNARSSLHYR FSAFGQELHL ELKPSAILSS

 121 HFIVQVLGKD GASETQKPEV QQCFYQGFIR NDSSSSVAVS TCAGLSGLIR TRKNEFLISP

 181 LPQLLAQEHN YSSPAGHHPH VLYKRTAEEK IQRYRGYPGS GRNYPGYSPS HIPHASQSRE

 241 TEYHHRRLQK QHFCGRRKKY APKPPTEDTY LRFDEYGSSG RPRRSAGKSQ KGLNVETLVV

 301 ADKKMVEKHG KGNVTTYILT VMNMVSGLFK DGTIGSDINV VVVSLILLEQ EPGGLLINHH

 361 ADQSLNSFCQ WQSALIGKNG KRHDHAILLT GFDICSWKNE PCDTLGFAPI SGMCSKYRSC

 421 TINEDTGLGL AFTIAHESGH NFGMIHDGEG NPCRKAEGNI MSPTLTGNNG VFSWSSCSRQ

 481 YLKKFLSTPQ AGCLVDEPKQ AGQYKYPDKL PGQIYDADTQ CKWQFGAKAK LCSLGFVKDI

 541 CKSLWCHRVG HRCETKFMPA AEGTVCGLSM WCRQGQCVKF GELGPRPIHG QWSAWSKWSE

 601 CSRTCGGGVK FQERHCNNPK PQYGGLFCPG SSRIYQLCNI NPCNENSLDF RAQQCAEYNS

 661 KPFRGWFYQW KPYTKVEEED RCKLYCKAEN FEFFFAMSGK VKDGTPCSPN KNDVCIDGVC

 721 ELVGCDHELG SKAVSDACGV CKGDNSTCKF YKGLYLNQHK ANEYYPVVLI PAGARSIEIQ

 781 ELQVSSSYLA VRSLSQKYYL TGGWSIDWPG EFPFAGTTFE YQRSFNRPER LYAPGPTNET

 841 LVFEILMQGK NPGIAWKYAL PKVMNGTPPA TKRPAYTWSI VQSECSVSCG GGYINVKAIC

 901 LRDQNTQVNS SFCSAKTKPV TEPKICNAFS CPAYWMPGEW STCSKACAGG QQSRKIQCVQ

 961 KKPFQKEEAV LHSLCPVSTP TQVQACNSHA CPPQWSLGPW SQCSKTCGRG VRKRELLCKG

1021 SAAETLPESQ CTSLPRPELQ EGCVLGRCPK NSRLQWVASS WSECSATCGL GVRKREMKCS

1081 EKGFQGKLIT FPERRCRNIK KPNLDLEETC NRRACPAHPV YNMVAGWYSL PWQQCTVTCG

1141 GGVQTRSVHC VQQGRPSSSC LLHQKPPVLR ACNTNFCPAP EKREDPSCVD FFNWCHLVPQ

1201 HGVCNHKFYG KQCCKSCTRK I
```

ADAMTS-18 is a disintegrin metalloproteinase with thrombospondin motifs, with binding domain at its C-terminal end. The 385 amino acid fragment of ADAMTS-18 (AD-18F) was identified using a peptide phage display library and GPIIIa(49-66) of the platelet integrin GPIIIa as the bait (Li et al., "C-terminal ADAMTS-18 Fragment Induces Oxidative Platelet Fragmentation, Dissolves Platelet Aggregates and Protects Against Carotid Artery Occlusion and Cerebral Stroke," *Blood* doi:10.1182/blood-2008-07-170571 (2009), prepublished online, which is hereby incorporated by reference in its entirety).

ADAMTS-18 is secreted and cleaved following thrombin activation (damage) of endothelial cells. It induces oxidative platelet fragmentation in an identical kinetic fashion as anti-GPIIIa(49-66) antibody. Thrombin produces a 45 kD terminal fragment similar to the ADAMTS-18, 385 amino acid fragment (i.e. AD-18F) (SEQ ID NO:10). AD-18F fragment also displays the desirable properties such as high affinity binding for GPIIIa(49-66), the ability to induce complement-independent platelet oxidative fragmentation and platelet death. This fragment, AD-18F, is an important endogenous regulator of arterial platelet thrombus formation, because an antibody against it, shortens the mouse tail vein bleeding time (Li et al., "C-terminal ADAMTS-18 Fragment Induces Oxidative Platelet Fragmentation, Dissolves Platelet Aggregates and Protects Against Carotid Artery Occlusion and Cerebral Stroke," *Blood* doi:10.1182/blood-2008-07-170571 (2009), prepublished online, which is hereby incorporated by reference in its entirety). Similar proteins or peptides with the ability to induce complement-independent platelet oxidative fragmentation and platelet death can be identified using the peptide phage display library and GPIIIa(49-66) as bait.

Thrombi-specific homing agents specifically target component molecules i.e., markers found in blood clots or components that are involved in generation of a blood clot. Exemplary targets of these thrombi-specific homing agents are fibrin, activated platelets, GPIIb/IIIa, P-selectin, tissue factor, tissue factor VIIA complex. The thrombi-specific homing agent can be an antibody raised against a desired target in a blood clot or against components involved in generation of a blood clot. These homing agents may reduce the side effects (e.g. thrombocytopenia, bleeding) by specifically directing the therapeutic agent to blood clots.

In one embodiment, the homing agent is the 1$^{st}$ kringle of plasminogen (which binds avidly to the C-terminal lysines of partially digested fibrin). One example of a therapeutic agent with 1$^{st}$ kringle of plasminogen as a homing agent is scFv-A11-Linker-kringle-1 (SLK) where the scFv antibody is linked to the 1$^{st}$ kringle of plasminogen. SLK has the following amino acid sequence (SEQ ID NO: 12), (linker sequence is underlined (scFv-A11 (242 aa)+linker (20 aa)+kringle-1 (78 aa)=340aa)):

```
  1 MAEVQLLESG GGLVQPGGSL RLSCAASGFT FSSYAMSWVR QAPGKGLEWV SSITSTGMET

 61 RYADSVKGRF TISRDNSKNT LYLQMNSLRA EDTAVYYCAK GKSHFDYWGQ GTLVTVSSGG

121 GGSGGGGSGG GGSTDIQMTQ SPSSLSASVG DRVTITCRAS QSISSYLNWY QQKPGKAPKL

181 LIYTASFLQS GVPSRFSGSG SGTDFTLTIS SLQPEDFATY YCQQRKSYPR TFGQGTKVEI

241 KRGSTSGGST SGGSTSGSGS GICKTGNGKN YRGTMSKTKN GITCQKWSST SPHRPRFSPA

301 THPSEGLEEN YCRNPDNDPQ GPWCYTTDPE KRYDYCDILE
```

This active SLK could bind to both platelet GPIIIa(49-66) and fibrin. Experiments suggest that it is better than scFv-targeting agent (A11) alone, since it reopens a carotid artery thrombus 4 hrs after cessation of blood flow as opposed to 2 hrs with scFv-A11 alone. scFv-A11 has the following amino acid sequence (SEQ ID NO: 13):

```
  1 MAEVQLLESG GGLVQPGGSL RLSCAASGFT FSSYAMSWVR QAPGKGLEWV SSITSTGMET

 61 RYADSVKGRF TISRDNSKNT LYLQMNSLRA EDTAVYYCAK GKSHFDYWGQ GTLVTVSSGG

121 GGGSGGGGSG GGGTDIQMTQ SPSSLSASVG DRVTITCRAS QSISSYLNWY QQKPGKAPKL

181 LIYTASFLQS GVPSRFSGSG SGTDFTLTIS SLQPEDFATY YCQQRKSYPR TFGQGTKVEI

241 KR
```

The homing agent can bind to fibrin or to activated platelets. When platelets are circulating through vessels with an intact, healthy endothelium, the platelets remain in their original, inactivated state. The absence of activating factors and the release of prostacyclin (prostaglandin I2) by the healthy endothelium supports this state. However, for example, when a platelet encounters a break in the endothelium, certain molecules trigger its activation. One such molecule is collagen, which is characteristically found almost everywhere except inside a blood vessel. Thromboxane A2, ADP, and thrombin are other factors that trigger the same platelet activation (Zucker et al., "Platelet Activation," *Arteriosclerosis* 5(1):2-18 (1985); Messmore et al., "Molecular Markers of Platelet Activation," *Semin Thromb Hemost* 10(4): 264-9 (1984); Mustard et al., "Platelet Activation—an Overview," *Agents Actions Suppl* 21:23-36 (1987), which are hereby incorporated by reference in their entirety). Activation of platelets is marked by exocytosis of the dense granules and alpha granules, activation of the membrane enzyme phospholipase A2 leading to the formation of thromboxane A2 (TXA2), change in shape to a more amorphous form with projecting fingers, adhesion to other platelets and to collagen under the endothelium, and formation of a platelet plug.

In another embodiment, the homing agent is PAC-1 antibody or binding portions thereof. It recognizes an epitope on the IIb-IIIa complex critical for fibrinogen binding. PAC-1 is an IgM antibody. PAC-1 heavy chain has the following amino acid sequence (SEQ ID NO:14)

```
  1 QVQLKQSGPG LVQPSQSLSI TCTVSGFSLT SYGVHWVRLS PGKGLEWLGV IWSGGSTDYN

 61 AAFISRLSIS KDNSKSQVFF KMNSLQANDT GIYYCARRSP SYYRYDGAGP YYAMDYWGQG

121 TSVTVSS
```

PAC-1 has the following light chain amino acid sequence (SEQ ID NO:15).

```
  1 DVLMTQTPLS LPVSLGDQAS ISCRSSQSIV HSNGNTYLEW YLQKPGQSPK LLIYKVSNRF

 61 SGVPDRFTGS GSGTDFTLKI SRVEAEDLGV YYCWQGSHVP YTFGGGTKLE IK
```

PAC-1 binds only to the activated form of the activated platelet GPIIb-IIIa complex (Shattil et al., "Changes in the Platelet Membrane Glycoprotein IIb-IIIa Complex During Platelet Activation," *J Biol Chem* 260:1 1107 (1985), which is hereby incorporated by reference in its entirety).

Other suitable targeting as well as homing agents can be discovered through techniques which are well known in the art. Such techniques include phage display or screening of peptide libraries. Aptamers, which are oligonucleotides that can bind to selected targets, and peptidomimetics, which are small organic molecules intended to mimic peptides with known affinities, can also be used as targeting or homing agents.

The therapeutic agent can also include a linker connecting the GPIIIa(49-66)-specific targeting agent and the homing agent. In a preferred embodiment, the linker connecting the GPIIIa(49-66)-specific targeting agent and the homing agent has the amino acid sequence of $(GSTSG)_3$ SGSGI (SEQ ID NO: 16). The therapeutic agent can further contain a short linker sequence coupling the portion of the targeting agent to the portion of the homing agent. Preferred linker sequences include glycine-rich (e.g. $G_3S_{2-3}$) or serine-rich (e.g. $GS_N$) linker sequences. Also suitable are the flexible linkers derived from an immunoglobulin, as disclosed in U.S. Pat. No. 5,516,637 to Huang et al, which is hereby incorporated by reference in its entirety.

The present invention also encompasses multispecific therapeutic agents. In this aspect of the present invention, the therapeutic agents can be derivatized or linked to more than one other targeting agent to generate multispecific molecules. These bind to two or more than two similar and/or different binding sites and/or target molecules on the platelets, in order to achieve the desired effect of inducing platelet fragmentation. Similarly, multiple homing agents targeting affected/afflicted cell types or tissues could be attached to the targeting agents of the present invention such that the therapeutic molecules could home to multiple cell types or tissues that are affected by thrombocytopenia.

The antibodies and proteins of the present invention include "binding portions" of the antibodies and proteins described above. A "binding portion" is a fragment, variant, analog, or chemical derivative of the subject antibody or protein, which terms are defined below. A binding portion retains at least a part of the amino acid sequence of the antibody or protein of interest, which permits its utility in accordance with the present invention, namely, induction of platelet fragmentation by GPIIIa(49-66) targeting and thrombi-specific homing agents. This specificity can readily be quantified by means of the techniques disclosed in the present invention and also by techniques known to those of skill in the art.

A "fragment" of the antibodies and proteins disclosed herein refers to any subset of the molecule, that is, a shorter peptide.

A "variant" of the antibodies or proteins refers to a molecule which is substantially similar either to the entire antibody or protein or a fragment thereof. Variant peptides may be conveniently prepared by direct chemical synthesis of the variant peptide, using methods well known in the art.

Alternatively, amino acid sequence variants of the antibodies and proteins of the present invention can be prepared by mutations in DNA molecules which encode the antibody or protein of interest. Such variants include, for example, deletions, insertions, or substitutions of residues within the amino acid sequences of the GPIIIa(49-66) targeting and thrombi-specific homing agents. Any combination of deletion, insertion, and substitution may be made to arrive at the final construct, provided that the final construct possesses the desired activity.

An "analog" of the antibodies or proteins refers to a non-natural molecule which is substantially similar to either the entire antibody or peptide or to an active fragment thereof.

A "chemical derivative" of an antibody or protein contains additional chemical moieties which are not normally part of the amino acid sequence of the antibody. Covalent modifications of the amino acid sequence are included within the scope of this invention. Such modifications may be introduced into the antibody or protein derivatives by reacting targeted amino acid residues from the protein with an organic derivatizing agent that is capable of reacting with selected side chains or terminal residues.

As used herein, the term "antibody" is meant to include intact immunoglobulins derived from natural sources or from recombinant sources, as well as immunoreactive portions (i.e. binding portions) of intact immunoglobulins. The antibodies of the present invention may exist in a variety of forms including, for example, polyclonal antibodies, monoclonal antibodies, intracellular antibodies ("intrabodies"), antibody fragments (e.g. Fv, Fab and F(ab)2), as well as single chain antibodies (scFv), chimeric antibodies, and humanized antibodies (Ed Harlow and David Lane, USING ANTIBODIES: A LABORATORY MANUAL (Cold Spring Harbor Laboratory Press, 1999); Houston et al., "Protein Engineering of Antibody Binding Sites: Recovery of Specific Activity in an Anti-Digoxin Single-Chain Fv Analogue Produced in *Escherichia coli*," *Proc Natl Acad Sci USA* 85:5879-5883 (1988); Bird et al, "Single-Chain Antigen-Binding Proteins," *Science* 242:423-426 (1988), which are hereby incorporated by reference in their entirety). In a preferred embodiment, the antibodies of the present invention can be single chain antibodies (scFv).

In addition to whole antibodies, the present invention encompasses binding portions of such antibodies. Such binding portions include the monovalent Fab fragments, Fv fragments (e.g., single-chain antibody, scFv), and single variable $V_H$ and $V_L$ domains, and the bivalent $F(ab')_2$ fragments, Bis-scFv, diabodies, triabodies, minibodies, etc. These antibody fragments can be made by conventional procedures, such as proteolytic fragmentation procedures, as described in James Goding, MONOCLONAL ANTIBODIES:PRINCIPLES AND PRACTICE 98-118 (Academic Press, 1983) and Ed Harlow and David Lane, ANTIBODIES: A LABORATORY MANUAL (Cold Spring Harbor Laboratory, 1988), which are hereby incorporated by reference in their entirety, or other methods known in the art.

Methods for monoclonal antibody production may be effected by the techniques described herein or other well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of a mammal which has been previously immunized with the antigen of interest (i.e., GPIIIa(49-66) peptide). The antibody-secreting lymphocytes are then fused with myeloma cells or transformed cells, thereby producing an immortal, immunoglobulin-secreting cell line (Milstein and Kohler, "Derivation of Specific Antibody-Producing Tissue Culture and Tumor Lines by Cell Fusion," *Eur. J. Immunol.* 6:511 (1976), which is hereby incorporated by reference in its entirety). The resulting fused cells, or hybridomas, are cultured, and screened for the production of the desired monoclonal antibodies. Colonies producing such antibodies are cloned, and grown either in vivo or in vitro to produce large quantities of antibody. Alternatively, monoclonal antibodies can be made using recombinant DNA methods as described in U.S. Pat. No. 4,816,567 to Cabilly et al., which is hereby incorporated by reference in its entirety. The polynucleotides encoding a monoclonal antibody are isolated from mature B-cells or hybridoma cells. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries (McCafferty et al., "Phage Antibodies: Filamentous Phage Displaying Antibody Variable Domains," *Nature* 348:552-554 (1990); Clackson et al., "Making Antibody Fragments using Phage Display Libraries," *Nature* 352:624-628 (1991); and Marks et al., "By-Passing Immunization. Human Antibodies from V-Gene Libraries Displayed on Phage," *J Mol Biol* 222:581-597 (1991), which are hereby incorporated by reference in their entirety).

The monoclonal antibody of the present invention can be a humanized antibody. Such antibodies are used therapeutically to reduce antigenicity and human anti-mouse antibody responses when administered to a human subject. A human antibody is an antibody produced by a human or an antibody having an amino acid sequence corresponding to an antibody produced by a human. An antibody can be humanized by substituting the complementarity determining region (CDR) of a human antibody with that of a non-human antibody (e.g. mouse, rat, rabbit, hamster, etc.) having the desired specificity, affinity, and capability (Jones et al., "Replacing the Complementarity-Determining Regions in a Human Antibody With Those From a Mouse," *Nature* 321:522-525 (1986); Riechmann et al., "Reshaping Human Antibodies for Therapy," *Nature* 332:323-327 (1988); Verhoeyen et al., "Reshaping Human Antibodies: Grafting an Antilysozyme Activity," *Science* 239:1534-1536 (1988), which are hereby incorporated by reference in their entirety). Humanized antibodies can be produced using various techniques known in the art. Immortalized human B lymphocytes immunized in vitro or isolated from an immunized individual that produce an antibody directed against a target antigen can be generated (See e.g. Reisfeld et al., MONOCLONAL ANTIBODIES AND CANCER THERAPY 77 (Alan R. Liss ed., 1985) and U.S. Pat. No. 5,750,373 to Garrard, which are hereby incorporated by reference in their entirety). Also, the humanized antibody can be selected from a phage library, where that phage library expresses human antibodies (Vaughan et al., "Human Antibodies with Sub-Nanomolar Affinities Isolated from a Large Non-immunized Phage Display Library," *Nature Biotechnology*, 14:309-314 (1996); Sheets et al., "Efficient Construction of a Large Nonimmune Phage Antibody Library: The Production of High-Affinity Human Single-Chain Antibodies to Protein Antigens," *Proc Nat'l Acad Sci U.S.A.* 95:6157-6162 (1998); Hoogenboom et al., "By-passing Immunisation. Human Antibodies From Synthetic Repertoires of Germline VH Gene Segments Rearranged In Vitro," *J Mol Biol* 227:381-8 (1992); Marks et al., "By-passing Immunization. Human Antibodies from V-gene Libraries Displayed on Phage," *J Mol Biol* 222:581-97 (1991), which are hereby incorporated by reference in their entirety). Humanized antibodies can also be made in transgenic mice containing human immunoglobulin loci that are capable upon immunization of producing the full repertoire of human antibodies in the absence of endogenous immunoglobulin production. This approach is described in U.S. Pat. No. 5,545,807 to Surani et al.; U.S. Pat. No. 5,545,806 to Lonberg et al.; U.S. Pat. No. 5,569,825 to Lonberg et al.; U.S. Pat. No. 5,625,126 to Lonberg et al.; U.S. Pat. No. 5,633,425 to Lonberg et al.; and U.S. Pat. No. 5,661,016 to Lonberg et al., which are hereby incorporated by reference in their entirety Procedures for raising polyclonal antibodies are also well known. Typically, such antibodies can be raised by administering the peptide or polypeptide containing the epitope of interest subcutaneously to New Zealand white rabbits which have been bled to obtain pre-immune serum. The antigens can be injected in combination with an adjuvant. The rabbits are bled approximately every two weeks after the first injection and periodically boosted with the same antigen three times every six weeks. Polyclonal antibodies are recovered from the serum by affinity chromatography using the corresponding antigen to capture the antibody. This and other procedures for raising polyclonal antibodies are disclosed in Ed Harlow and David Lane, USING ANTIBODIES: A LABORATORY MANUAL (Cold Spring Harbor Laboratory Press, 1988), which is hereby incorporated by reference in its entirety.

It may further be desirable, especially in the case of antibody fragments, to modify the antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Antibody mimics are also suitable for use in accordance with the present invention. A number of antibody mimics are known in the art including, without limitation, those known as monobodies, which are derived from the tenth human fibronectin type III domain ($^{10}$Fn3) (Koide et al., "The Fibronectin Type III Domain as a Scaffold for Novel Binding Proteins," *J Mol Biol* 284:1141-1151 (1998); Koide et al., "Probing Protein Conformational Changes in Living Cells by Using Designer Binding Proteins: Application to the Estrogen Receptor," *Proc Nat'l Acad Sci USA* 99:1253-1258 (2002), each of which is hereby incorporated by reference in its entirety); and those known as affibodies, which are derived from the stable alpha-helical bacterial receptor domain Z of staphylococcal protein A (Nord et al., "Binding Proteins Selected from Combinatorial Libraries of an alpha-helical Bacterial Receptor Domain," *Nature Biotechnol.* 15(8):772-777 (1997), which is hereby incorporated by reference in its entirety).

Another aspect of the present invention is related to therapeutic composition containing the therapeutic agent of the present invention as described supra and a pharmaceutically acceptable carrier or other pharmaceutically acceptable components.

As will be apparent to one of ordinary skill in the art, administering any of the agents of the present invention may be carried out using generally known methods. Typically, the agents of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The agents of the present invention may be orally administered, for example, with an inert diluent, with an assimilable edible carrier, enclosed in hard or soft shell capsules, compressed into tablets, or incorporated directly with the food of the diet. Such compositions and preparations should contain at least 0.1% of active compound. The percentage of the agent in these compositions may, of course, be varied and may conveniently be between about 2% to about 60% of the weight of the unit. The amount of active agent in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These active agents may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The agents of the present invention may also be administered directly to the airways in the form of an aerosol. For use as aerosols, the agents of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Another aspect of the present invention pertains to methods of treating thromboembolic disorders in a subject by administering a therapeutic agent which comprises a GPIIIa(49-66)-specific targeting agent and a homing agent directed to thrombi and linked to the GPIIIa(49-66)-specific targeting agent.

Thromboembolic disorders that can be treated according to the methods of the present invention include, without limitation, arterial thrombosis, cerebral infarction, myocardial infarction, stroke, pulmonary embolism, ischemic diseases. In carrying out this method of treatment, the therapeutic agent can be engineered, formulated, and administered in substantially the manner noted above.

Suitable subjects to be treated in accordance with the present invention are subjects that are at risk of developing or have developed thromboembolic disorders. Such subjects include human and non-human animals, preferably mammals. Exemplary mammalian subjects include, without limitation, humans, non-human primates, dogs, cats, rodents, cattle, horses, and sheep.

Another aspect of the present invention relates to methods of inducing platelet fragmentation in a subject by administering a therapeutic agent which comprises a GPIIIa(49-66)-specific targeting agent and a homing agent directed to thrombi and linked to the GPIIIa(49-66)-specific targeting agent to the subject. In carrying out this method of treatment, the therapeutic agent can be engineered, formulated, and administered in substantially the manner noted above. Subjects suitable for such treatment are noted above.

The present invention is illustrated, but not limited, by the following examples.

EXAMPLES

Example 1

Materials

All reagents were obtained from Sigma (St. Louis, Mo.) unless otherwise designated. ADAMTS-18 peptide conjugated to Biotin, Bio-VQTRSVHCVQQGRPSSSC-OH (SEQ ID NO: 17), ADAMTS-18 scrambled peptide, Bio-VQTRSVQVHCQGRPSSSC-OH (SEQ ID NO: 18), GPIIIa(49-66) conjugated to Biotin (Bio-CAPESIEFPVSEARVLED) (SEQ ID NO: 19) and GPIIIa(49-66) (CAPESIEFPVSEARVLED) (SEQ ID NO: 9) were synthesized by Biosynthesis, Inc. (Lewisville, Tex.). Human scFv Tomlinson I+J libraries were obtained from the MRC Gene Service (Cambridge, UK). scFv-A11 was made from a Human scFv phage surface display monoclonal library as described in Li et al., "Platelet Fragmentation Requires a Specific Structural Conformation of Human Monoclonal Antibody Against β3 Integrin," *J Biol Chem* 283:3224-3230 (2008), which is hereby incorporated by reference in its entirety. Anti-N-terminal ADAMTS-18 is a polyclonal antibody, kindly provided by Dr. Andrew J. Connolly, Stanford Medical School. *E. coli* strains Rosseta, plasmid pET-29a and Ni-NTA agarose resin were from Novagen (Nottingham, UK). Restriction enzymes were obtained from New England Biolabs (Beverly, Mass.).

Example 2

Mice

Platelet counts were measured by phase-contrast microscopy as previously described (Nardi et al., "Complement-independent Ab-induced Peroxide Lysis of Platelets Requires 12-lipoxygenase and a Platelet NADPH Oxidase Pathway," *J Clin Invest* 113:973-980 (2004), which is hereby incorporated by reference in its entirety). GPIIIa−/− mouse platelets with C57/BL6 background and BALB/C mice were purchased from Jackson Laboratory and genotype confirmed by PCR. Swiss Webster mice were obtained from Jackson Laboratory.

Example 3

Expression Constructs

Full length ADAMTS-18 cDNA coding sequence was cloned into mammalian expression vector pBudCE4.1 from Invitrogen (Carlsbad, Calif. 92008). Two constructs with and without the His-tag were made. Three constructs were made to express the C-terminal domains of ADAMTS-18 in pGEX-4T-2 vector from GE Healthcare (Piscataway, N.J. 08855). These constructs express the C terminal fragments of ADAMTS-18. The first fragment is made of residues 837-1221 (385 aa) (AD-18F) (SEQ ID NO:10). The second fragment is made of residues 1034-1221 (188 aa) with the following amino acid sequence (SEQ ID NO: 20):

```
  1 LPRPELQEGC VLGRCPKNSR LQWVASSWSE CSATCGLGVR KREMKCSEKG FQGKLITFPE
 61 RRCRNIKKPN LDLEETCNRR ACPAHPVYNM VAGWYSLPWQ QCTVTCGGGV QTRSVHCVQQ
121 GRPSSSCLLH QKPPVLRACN TNFCPAPEKR EDPSCVDFFN WCHLVPQHGV CNHKFYGKQC
181 CKSCTRKI
```

The third fragment is made of residues 1156-1221 (66 aa), with the following amino acid sequence (SEQ ID NO: 21):

```
 1 PSSSCLLHQK PPVLRACNTN FCPAPE-
KRED PSCVDFFNWC HLVPQHGVCNH HKFYGKQCCK
61 SCTRKI
```

The 385 aa construct was also scrambled at residues 1149 to 1152 of ADAMTS-18 in which HCVQQ was mutated to QVHCQ (sc 385 aa) with the following amino acid sequence (SEQ ID NO: 22):

```
  1 NETLVFEILM QGKNPGIAWK YALPKVMNGT PPATKRPAYT WSIVQSECSV SCGGGYINVK
 61 AICLRDQNTQ VNSSFCSAKT KPVTEPKICN AFSCPAYWMP GEWSTCSKAC AGGQQSRKIQ
121 CVQKKPFQKE EAVLHSLCPV STPTQVQACN SHACPPQWSL GPWSQCSKTC GRGVRKRELL
181 CKGSAAETLP ESQCTSLPRP ELQEGCVLGR CPKNSRLQWV ASSWSECSAT CGLGVRKREM
241 KCSEKGFQGK LITFPERRCR NIKKPNLDLE ETCNRRACPA HPVYNMVAGW YSLPWQQCTV
301 TCGGGVQTRS VQVHCQGRPS SSCLLHQKPP VLRACNTNFC PAPEKREDPS CVDFFNWCHL
361 VPQHGVCNHK FYGKQCCKSC TRKI
```

Example 4

Purification of GST-ADAMTS-18 Fragments from *E. coli*

*Escherichia coli* BL 21 transformed with the pGEX-4T-2 construct plasmid were grown at 37° C. in LB medium with 50 μg/ml to an $OD_{600}$ of 0.5. IPTG (0.2 mM) was then added to induce expression of the GST fusion gene in culture overnight, at 25° C. Cells were harvested, resuspended in phosphate-buffered saline, and sonicated with a sonicator. The cell debris was removed by centrifugation. The cell-free extract was loaded onto glutathione-agarose beads from Sigma (Sigma-Aldrich, Mo. 63178). The purified GST proteins were then examined by SDS-PAGE.

Example 5

Assay of ADAMTS-18

A standard curve was prepared with the ADAMTS-18 C-terminal 385 aa (AD-18F) peptide applied overnight at 4° C. to a microtiter plate in 0.01 M bicarbonate buffer, pH 9.5. The plate was washed and blocked twice with TBS+1% BSA and incubated overnight at 4° C. A polyclonal rabbit anti-ADAMTS-18 mer IgG (>93% specificity, determined by Ag absorption) was then applied overnight. The plate was washed as above and then treated with donkey anti-rabbit IgG. A standard curve was sensitive at 10 ng. Test material was assayed at varying dilutions, at which preimmune sera or second antibody alone had no effect.

Example 6

Affinity Purification of Anti-Platelet GPIIIa(49-66)

Peptide GPIIIa(49-66) (CAPESIEFPVSEARVLED) (SEQ ID NO: 9) was coupled to an affinity column with the heterobifunctional cross-linker sulfo-succinimidyl 4-(N-maleimidomethyl)cyclohexane-1 carboxylase as recommended by the manufacturer (Pierce Biotechnology, Inc.). This cross-linked the resin with the $NH_2$-terminal cysteine of the peptide which was then incubated with 0.4 ml of platelet affinity-purified IgG (Karpatkin et al., "Sequestration of Anti-platelet GPIIIa Antibody in Rheumatoid Factor Immune Complexes of Human Immunodeficiency Virus 1 Thrombocytopenic Patients," *Proc Nat'l Acad Sci USA* 92:2263-2267 (1995), which is hereby incorporated by reference in its entirety) overnight at 4° C. The column was then washed, eluted at pH 2.5 and neutralized as described (Karpatkin et al., "Sequestration of Anti-platelet GPIIIa Antibody in Rheumatoid Factor Immune Complexes of Human Immunodeficiency Virus 1 Thrombocytopenic Patients," *Proc Nat'l Acad Sci USA* 92:2263-2267 (1995), which is hereby incorporated by reference in its entirety).

Example 7

Generation of Human scFv Monoclonal Anti-GPIIIa(49-66) Antibodies by Phage Display Human scFv (single chain fragment variable region) Tomlinson I+J libraries were used to generate human anti-GPIIIa (49-66) monoclonal antibody. Each library contains over 100 million different scFv fragments cloned in phage-mid vector pIT2 (Clackson et al., "Making Antibody Fragments Using Phage Display Libraries," *Nature* 352(6336):624-8 (1991); Nissim et al., "Antibody Fragments From a 'Single Pot' Phage Display Library as Immunochemical Reagents," *EMBO J* 13(3):692-8 (1994); and Griffiths et al., "Isolation of High Affinity Human Antibodies Directly From Large Synthetic Repertoires," *EMBO J* 13(14):3245-60 (1994), which are hereby incorporated by reference in their entirety).

Figure 1:
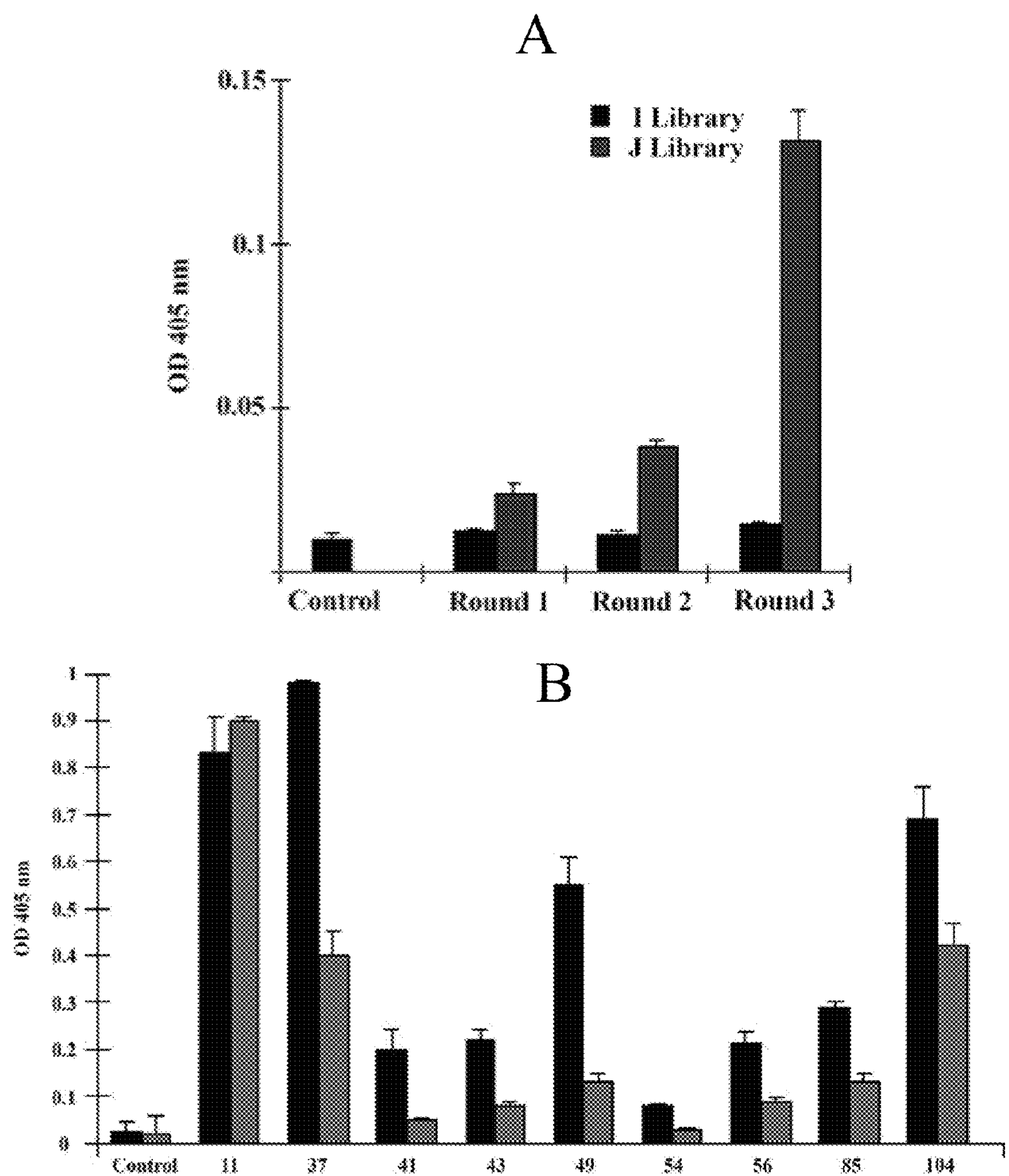
FIGS. 1A-B show data regarding the generation of monoclonal anti-GPIIIa(49-66) human scFv antibodies using phage display.

The libraries were used to screen against a biotin conjugated GPIIIa(49-66) peptide. After each round of screening, binding activity of phage clones were examined by ELISA (FIG. 1A). After a second round of panning, positive phage clones from library J were enriched. Since the binding activity of phage clones from library I was not increased after three rounds of panning, clones from library J were screened. After three rounds of panning, scFv clones were randomly chosen from the bacterial plate and individual scFv antibodies made from each clone. The binding activity to GPIIIa(49-66) was examined by an ELISA (FIG. 1B). All nine clones were found to bind to GPIIIa(49-66) at varying activity, with OD reading varying from 3 to 40 times background (FIG. 1B).

Example 8

Expression of scFv-A11 and SLK Fragment in *E. coli* Hosts

Figure 2:
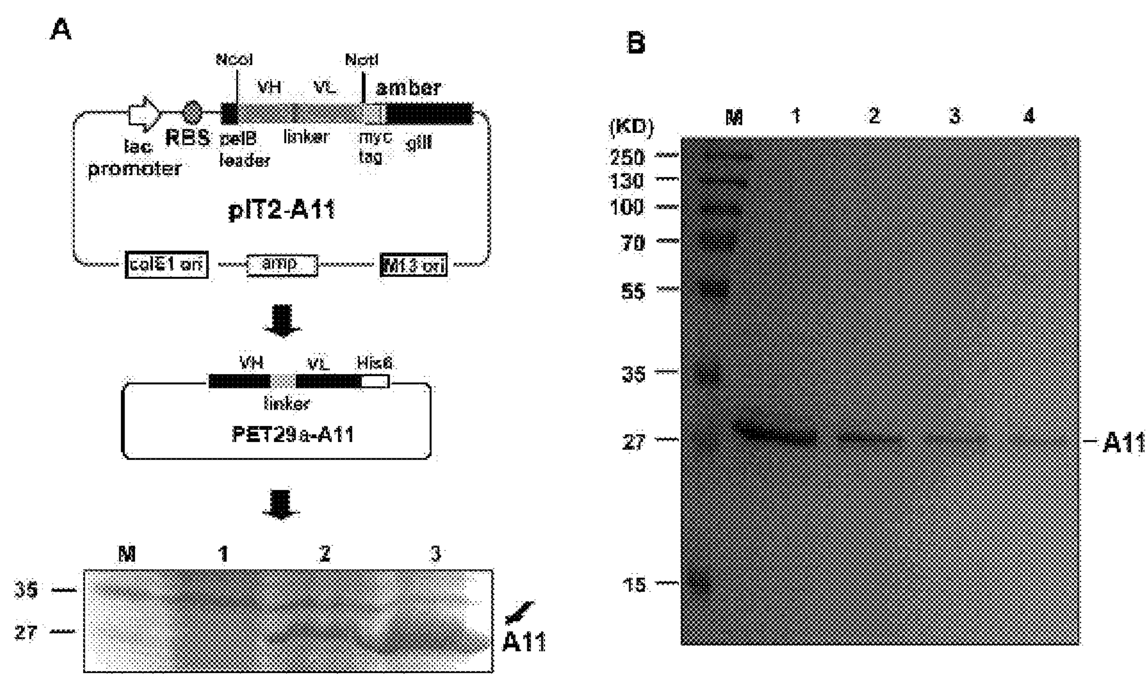
FIGS. 2A-B show the construction, expression, and purification of the soluble scFv-A11.

For large-scale expression of soluble scFv protein, the scFv gene fragment was digested with the Nco I and Not I restriction enzymes from the pIT2-A11 phagemid and cloned to the expression vector pET-29a (FIG. 2A). Upon induction with IPTG, this vector produces scFv-A11 soluble protein (~29 kD) tagged with a His-tag (FIG. 2A). After purification, the purity of the active scFv-A11 was evaluated by 12% SDS-PAGE and Commassie blue staining. The antibody fragment was visualized as a 29-kD band (FIG. 2B).

The scFv-A11 has 726 bp in DNA coding 242 amino acids (118 amino acids in the heavy chain; 15 amino acids in the linker and 109 amino acids in the light chain). The heavy and light chain variable regions were found to belong to human A7 and kappa gene family, respectively (FIG. 3A, B).

*E. coli* Rosetta cells transformed with the expression vector pET29a-scFv-A11 and pET29a-SLK were cultured in 1 L 2YT medium containing carbenicillin (50 μg/ml) and chloramphenicol (34 μg/ml) with shaking at 37° C. until the OD (600 nm) was 0.4-0.6. Production was induced by the addition of 1 mM IPTG, and the cells were allowed to incubate at 37° C. for 4 hrs with shaking Finally, cells were harvested and the pellets were frozen at −20° C. for storage.

Example 9

ELISA Assays

Figure 4:
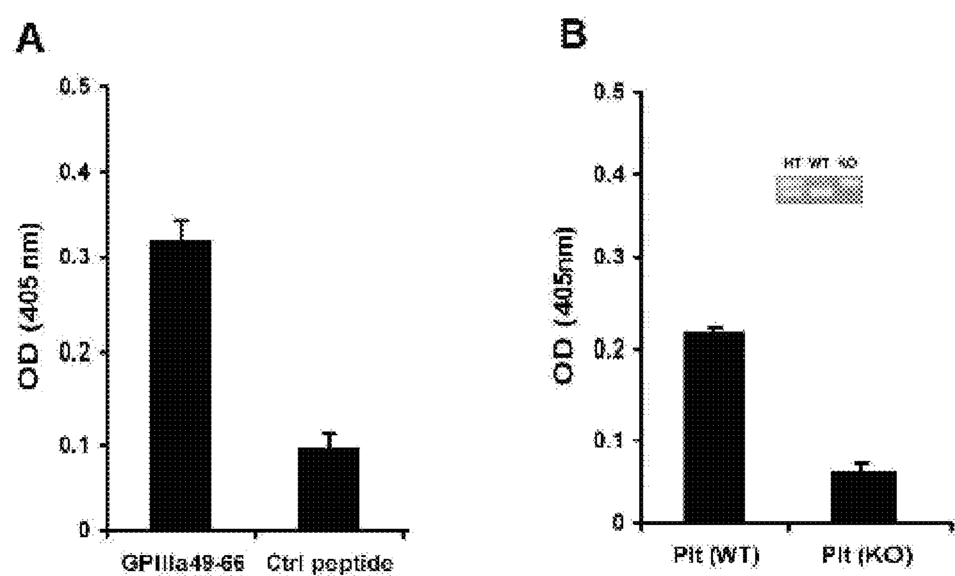
FIGS. 4A-B show that scFv-A11 specifically binds to platelet GPIIIa(49-66) in an ELISA assay. Soluble scFv was incubated on ELISA plate coated with different antigens including peptide GPIIIa(49-66). Irrelevant peptide is shown in FIG. 4A and platelets isolated from wild type mouse (WT) and GPIIIa−/− knock out mouse (KO) are shown in FIG. 4B. Bound scFv was detected by an ELISA using anti-His tag antibody.

Plastic microtiter plates (Corning Incorporated, NY) were coated with 20 μg/ml GPIIIa(49-66) or irrelevant peptide (IR) or platelets ($1\times10^6$/well) in 50 mmol/L $NaHCO_3$ buffer (pH 9.6) at 4° C. overnight. The plate was then blocked with blocking buffer (3% BSA in PBST, 0.1% Tween20) for 2 hours at RT. Soluble scFv or SLK with Histine tag were added to the plates and incubated for 1 hr at RT. scFv or SLK were detected with primary mouse anti-His tag antibodies and followed by secondary goat anti-mouse IgG/HRP. After washing thoroughly, ABTS was added per well for color development, and the absorbance was determined at 405 nm. The specificity of scFv-A11 Ab was evaluated by an ELISA with different antigens. It was found that the scFv-A11 bound to platelet GPIIIa(49-66) specifically (FIG. 4A, B).

For fibrin binding experiment, human fibrinogen (5 μg/ml) was coated onto the wells of a plastic microtiter plates and left overnight at 4° C. After blocking the exposed site with blocking buffer, the wells were incubated with a solution of phosphate-buffered saline containing human thrombin (1 NIH unit/ml) and $CaCl_2$ (20 mM) for 2 h at 37° C. Cross-linked fibrin clots on the wells were partially digested with plasmin for different time periods. Purified scFv-A11 and SLK in PBS were added to the wells at a final concentration of 500 nM (50 pmol/well). Binding of scFv-A11 or SLK to the partially digested fibrin was monitored with primary mouse anti-His tag antibodies and secondary goat anti-mouse IgG/HRP. After washing thoroughly, ABTS was added per well for color development and the absorbance was determined at 405 nm.

Example 10

Preparation of Platelet-Fibrinogen Aggregates In Vitro

To produce ADP-induced aggregates, $1\times10^7$ gel filtered platelets were incubated with 100 mg/ml fibrinogen and ADP (10 μM) for 30 minutes at 37° to create platelet aggregates. Excess reagents were removed by washing in PBS, and the number of platelets/aggregate counted. Collagen-induced aggregates were formed by incubating 1 μg/ml collagen (Helena Lab, Lubbock, Tex.) for 1 hr at 37° C. with intermittent shaking, followed by gravity sedimentation at room temperature for 30 min. The top 50% volume was removed, and the remainder of the platelet aggregate suspension added directly into Tyrodes buffer with testing reagents. Anti-GPIIIa(49-66) antibody (20 μg/ml) or AD-18F (35 μg/ml) was added for various time intervals and the remaining platelets/aggregate enumerated.

Example 11

Induction of Platelet Particle Formation

Gel-filtered normal platelets were prepared from platelet-rich plasma obtained from blood collected in 0.38% sodium citrate utilizing a sepharose 2B column preincubated with Tyrode's buffer (pH 7.4). $1\times10^7$ gel-filtered platelets/ml were either unlabeled or labeled with an anti-GPIIb-fluorescein isothiocyanate (FITC)-labeled antibody (3B2) or an anti-GPIIIa-FITC monoclonal antibody (Ancell, Bayport, Minn.) to 10 μg/ml for 30 min at 4° C., centrifuged at 1000 g×6 min at room temperature, and resuspended in Tyrodes buffer. Ten microliters of unlabeled or FITC-labeled platelets ($10^7$/ml) were then incubated with human scFv anti-GPIIIa(49-66) (5-40 μg/ml), affinity-purified anti-GPIIIa(49-66), or AD-18F (385 aa) (25-50 μg/ml), in 100 μl volume of Tyrodes buffer for 0-4 hr at 37° C. and then stored in an ice bucket prior to measurement of percentage of platelet particles by flow cytometry. Further particle formation was arrested by incubation at 0° C.

Example 12

Assay of Platelet Particle Formation

Fluorescent-labeled platelet particles were measured by flow cytometry, employing a FACScan (Becton-Dickinson, Mountain View, Calif.). Debris and dead cells were excluded using scatter gates. Only cells with low orthogonal light scattering were included in the sorting gates. Gates were adjusted for control platelets by exclusion of other blood cells. Fluorescently labeled intact platelets were monitored in the right upper quadrant with the Y axis measuring forward-scatter and the X axis measuring fluorescence. A shift in fluorescent particles from right upper quadrant to left upper and lower quadrants reflected the percentage of platelet particle induction of 10,000 counted platelets/particles.

Example 13

Assay of LDH

Lactate Dehydrgenase (LDH) was assayed employing the commercial LDH Kit supplied by Biotrin Diagnostics, Inc., Hemet, Calif.

Example 14

Assay of Platelet Oxidation

Gel-filtered platelets were loaded with 10 μM DCFH-DA for 30 min at 37° C. as described (Nardi et al., "Complement-independent, Peroxide Induced Antibody Lysis of Platelets in HIV-1-related Immune Thrombocytopenia," *Cell* 106:551-561 (2001), which is hereby incorporated by reference in its entirety) and challenged with control or anti-GPIIIa(49-66) IgG. Oxidation was quantified by measuring the increase in mean fluorescence with flow cytometry.

Example 15

Figure 5:
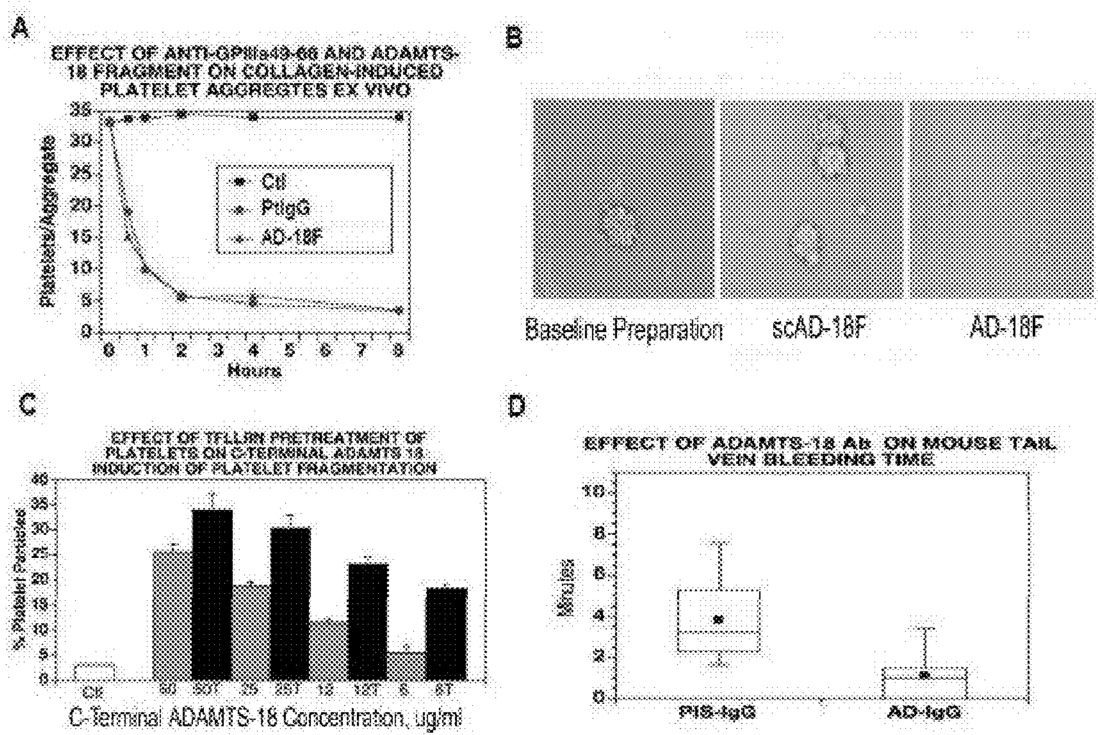
FIGS. 5A-D show the effect of a polyclonal anti-GPIIIa (49-66), an ADAMTS-18 385 amino acid ("aa") fragment (AD-18F), a control (scrambled ADAMTS-18 fragment (scAD-18F), or an inactive ADAMTS-18 66 aa fragment on disaggregation and destruction of ex vivo platelet aggregates and the effect of anti-ADAMTS-18 antibody on in vivo bleeding time.

Destruction of Platelet-Fibrinogen Aggregates In Vitro $1\times10^7$ platelets were incubated with 100 mg/ml fibrinogen and 10 μm ADP for 30 minutes with shaking at 37° C. to create platelet aggregates. Excess reagents were removed bycentrifugation at 1000×g for 2 minutes. The platelet aggregates were then resuspended in PBS on a counting chamber, and the number of platelets/aggregate was counted. Anti-GPIIIa(49-66) antibody was then added for various time intervals, and the remaining number of platelets/aggregate was enumerated. Both scFv-A11 and AD-18F fragment platelet-collagen- or -ADP-induced aggregates ex vivo (FIG. 5).

Example 16

Mouse Tail Bleeding Time

The mouse tail vein was severed 2 mm from its tip and blotted every 30 seconds on a circular sheet of filter paper to obtain an objective measurement. The variation of the bleeding time was recorded after absence of blood on the filter paper. Bleeding time differences were recorded by an unbiased observer and confirmed by 2 other observers.

Example 17

Figure 6:
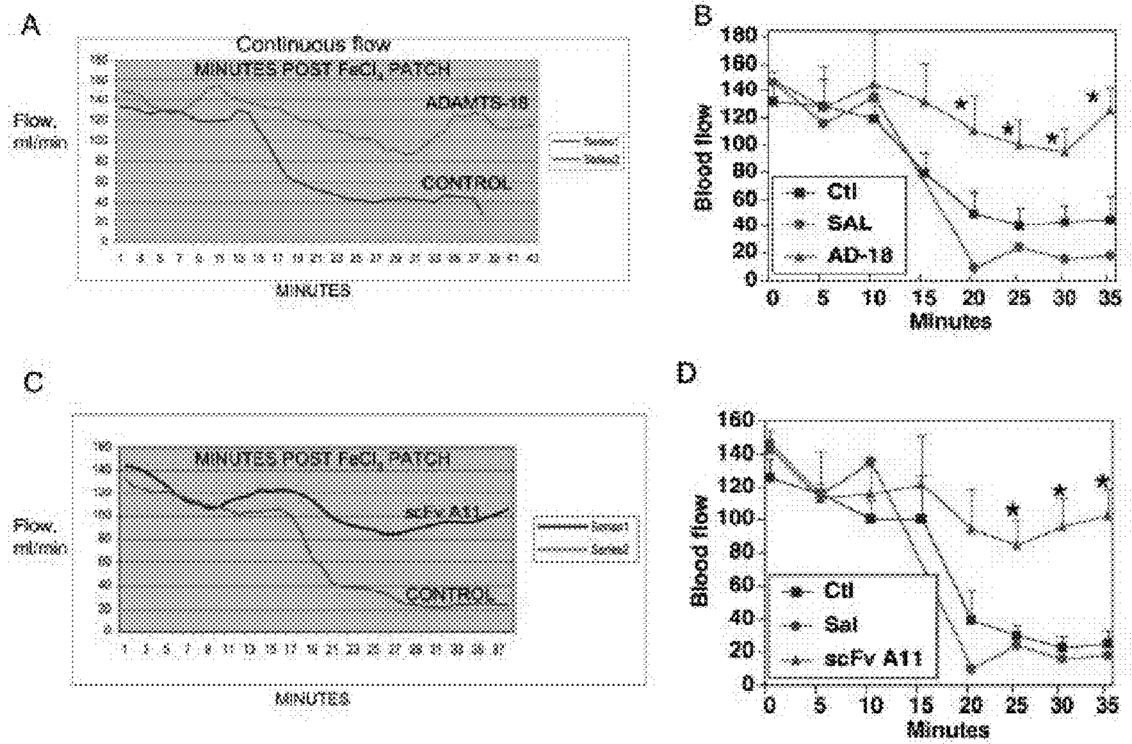
FIGS. 6A-D show the effect of AD-18F or scFv-A11 on inhibition of $FeCl_3$ induced carotid artery platelet thrombus formation.
Figure 7:
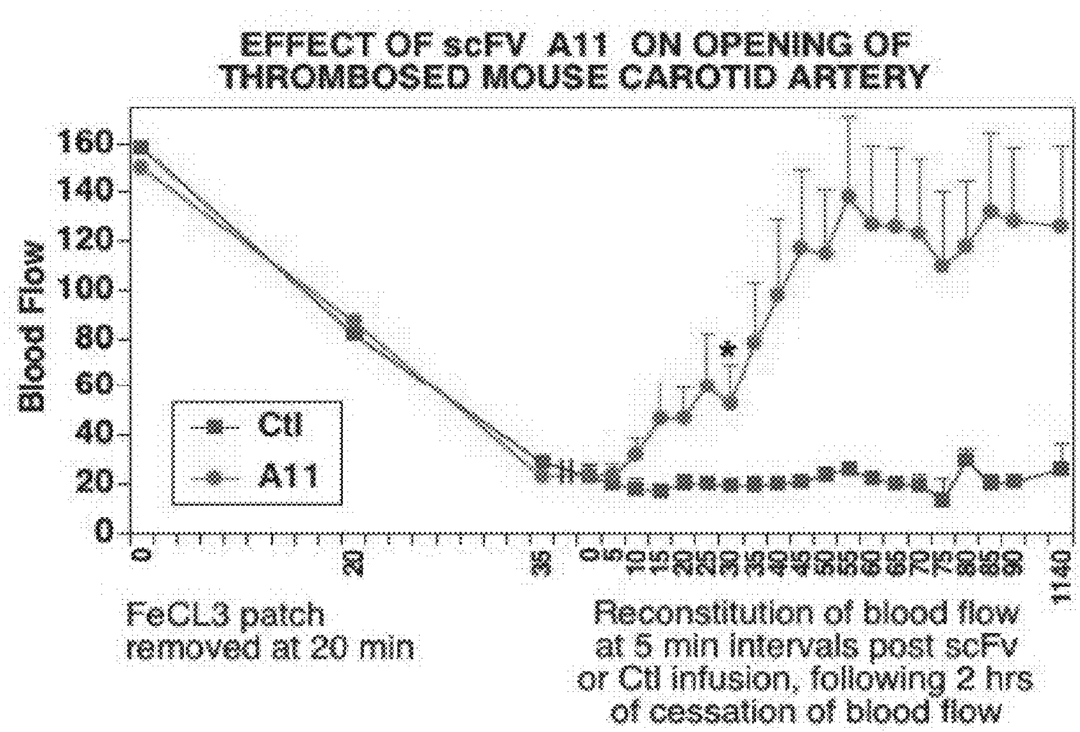
FIG. 7 shows that scFv-A11 reconstitutes blocked carotid artery thrombus blood flow 2 hrs after cessation of blood flow. The carotid artery of a mouse was dissected free of surrounding tissue and a $FeCl_3$ patch applied for 20 min, followed by rinsing. Blood flow was monitored with a Doppler flow apparatus. Cessation of blood flow was generally at 35 min. Two hrs after cessation of blood flow (vertical lines), the mice were infused i.v. with 25 μg of scFv-A11 or control Ab. There is a rapid re-onset of blood flow, 10-15 min after infusion. All time point differences at and after 30 min (*) were statistically significant by Student t test (P<0.04), n=4 in each group.

Carotid Artery Thrombus Formation $FeCl_3$-induced arterial injury was performed in 6 to 8-week-old Swiss Webster Mice. A 1×2-$mm^2$ strip of No. 1 Whatman filter paper (Fisher Scientific, Pittsburgh, Pa.) soaked in 10% $FeCl_3$ was dried and prepared for use. The right common carotid artery was exposed by blunt dissection, and a 4×8 mm paraffin strip was placed around the artery to isolate it from surrounding tissue. A Doppler flow probe (Model BPM2 Blood Perfusion Monitor; Vasamedics, St. Paul, Minn.) was positioned around the artery, 1 mm proximal to the bifurcation of the external carotid artery. The strip of filter paper was applied to the adventitial surface of the artery, 5 mm from the probe for 20 minutes. The filter paper was removed, the field was flushed with saline, and the blood flow continuously monitored and recorded at base line, start of injury, and each minute for 35 minutes.

scFv-A11 as well as AD-18F were investigated for their clinical use in the prevention or treatment of cerebral stroke as well as other arterial platelet thrombus disorders. Murine carotid artery injury with $FeCl_3$ induces a platelet carotid artery thrombus which leads to cessation of carotid artery flow (determined by Doppler). This can be prevented with scFv-A11 or AD-18F (FIG. 6). Surprisingly, the thrombus can be "dissolved" (oxidatively fragmented) 2 hrs after cessation of blood flow by scFv-A11 (FIG. 7). Both scFv-A11 and AD-18F can prevent as well as ameliorate murine middle cerebral artery stroke, neurologic damage, and brain function, without thrombocytopenia or brain hemorrhage.

Example 18

Post-Ischemic Stroke Model

Focal cerebral ischemia was induced by the intraluminal suture method using a procedure adapted from that previously described (Longa et al., "Reversible Middle Cerebral Artery Occlusion without Craniectomy in Rats," *Stroke;* 201: 84-91 (1989), which is hereby incorporated by reference in its entirety). A 3×0.2 mm polyethylene thread attached to a 9 mm 7/0 suture was inserted into the right internal carotid artery and advanced to the bifurcation of the middle cerebral artery. The obstruction was removed at 60-90 min. Mice were sacrificed at 48 hrs or 8 days. Mouse brains were dissected into 8 coronal planes at 1 mm intervals. Each section was stained red with triphenyltetrazolium chloride, fixed in 10% formalin. Unstained areas were defined as infarcted tissue. The sections were digitally photographed and the unstained area of infarct was computer calculated using an automated image analysis program (Image J 1.32, NIH). The sensorimotor behaviors were evaluated by performance on the postural reflex as previously described in Kiyota et al., "Postural Sway and Brain Potentials Evoked by Visual Depth Stimuli," *Int J Neurosci* 118 (7):935-53 (2008), which is hereby incorporated by reference in its entirety.

Example 19

Neurological Test Battery

Animals were evaluated on the following behavioral tests, 8 days after stroke onset, by methods previously described in detail (Quartermain et al., "Acute Enoxaparin Treatment Widens the Therapeutic Window for tPA in a Mouse Model of Embolic Stroke," *Neurol Res* 29:469-475 (2007), which is hereby incorporated by reference in its entirety).

In the postural reflex test, mice were held by the tail above the table and slowly lowered to the table edge to evaluate forelimb flexion. Neurologically, normal mice extend both forelimbs towards the edge. Mice with ischemic damage consistently flex the forelimb contralateral to the damaged hemisphere. Mice with mild deficit were given the score of 1, score of 2 was assigned for moderate deficit, and a score of 3 was given when the deficit was marked.

In the rotor rod test, an accelerating rotor-rod was used to measure the mouse's balance and motor coordination post operation. Each mouse was given three trials 15 min apart, with a 30 second adaptation at the beginning of the first trial. The rotation dial reading was increased from 1.5 to 10 with an accelerating rate of 0.5 every 15 seconds. The dial reading was recorded as the mouse falls. The time at falling from the rod was averaged for the tree trials.

In the traverse beam, motor behavior was evaluated using the traverse beam test adapted for mice. The apparatus consists of a wooden beam positioned above the bench top. At one end of the beam is an enclosed darkened goal box. A doorway provides access to the box from the beam. At the other end of the beam, a 300 W halogen lamp is mounted. Mice were trained to escape from the bright light by running to the opposite end and entering the darkened goal box. Performance was scored using the following scale: 1: mouse is unable to balance on the beam; 2: mouse is able to balance but cannot place limbs on the beam; 3: mouse traverses beam by dragging a limb; 4: mouse places limbs on the beam at least once during traverse; 5: mouse places limbs on the beam during 50% of the time; 6: mouse uses limbs during more than 50% of the time; 7: mouse traverses beam with no more than two-foot slips. Each mouse was given a total of five trials.

Example 20

Statistical Analysis

Data are present as mean±SD. The statistical comparisons were made by ANOVA (following a Newman-Keuls test), and differences were considered to be significant at $P<0.05$.

Example 21

Figure 8:
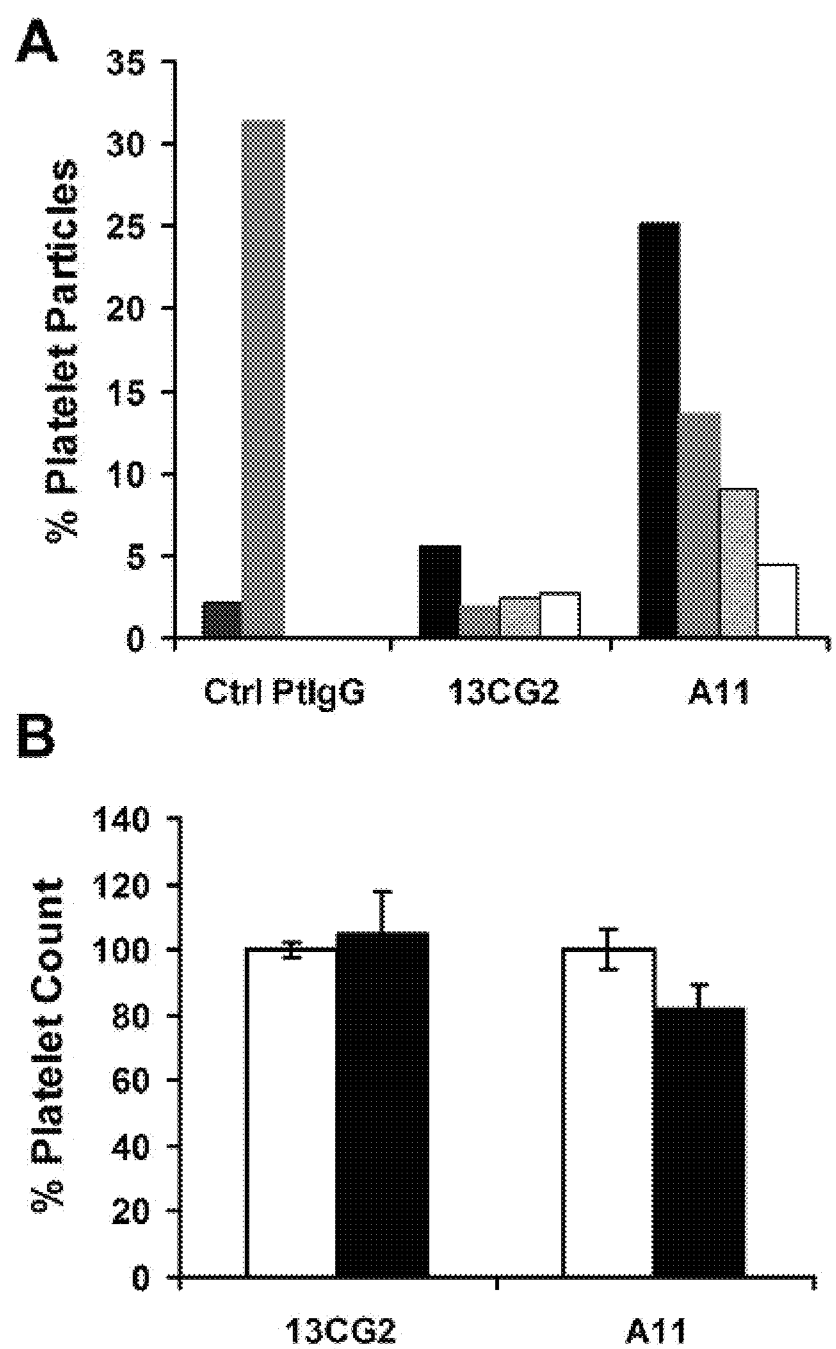
FIGS. 8A-B show the induction of platelet fragmentation by active scFv-A11.

Effect of scFv Antibodies on Platelet Fragmentation and Destruction of Platelet Aggregates Gel-filtered human platelets were incubated with various concentration of scFv-A11 antibody. The results demonstrated that active scFv-A11 Ab induces platelet fragmentation in the same manner as patient anti-GPIIIa(49-66) Ab, whereas irrelevant scFv had no effect on platelet fragmentation (FIG. 8A). In vivo, platelet count remained ~85% of normal range at 4 hr following scFv-A11 vs. control injection ($1.07\times10^6$ vs. $0.87\times10^6$, respectively, n=4) (FIG. 8B).

Experiments showed that not all clones induced platelet fragmentation (FIG. 9A) and the binding activity (FIG. 9B) did not correlate with platelet fragmentation. This suggested that a specific conformation induced by the antibody is more important than the avidity of binding. The findings were confirmed with separate clones by measuring the binding and ability to induce platelet fragmentation against a standard curve created with a clone that had a potent binding and functional antibody. The functional ability of clones to disaggregate/destroy ADP-induced in vitro platelet aggregates was also tested. All clones tested destroyed platelets aggregates in the same manner as antibody from an HIV-1 patient.

A series of mutant clones of scFv antibodies were generated by site directed mutagenesis as described in Li et al., "Platelet Fragmentation Requires a Specific Structural Conformation of Human Monoclonal Antibody Against β3 Integrin," *J Biol Chem* 283:3224-30 (2008), which is hereby incorporated by reference in its entirety. As described in the previous paragraph, it was found that the binding avidity did not correlate with the ability to induce platelet fragmentation. In order to investigate the requirements for modulating platelet fragmentation, mutations of positively charged amino acids were introduced in the heavy chains of various scFv clones. The binding activities of these mutants were analyzed by ELISA assays. The ability to induce platelet fragmentation were also analyzed. The data revealed that the positively charged amino acids may affect antibody function. Molecular modeling of these mutants revealed that the ability to induce platelet fragmentation is affected by side chain orientation of positively charged amino acids (Li et al., "Platelet Fragmentation Requires a Specific Structural Conformation of Human Monoclonal Antibody Against β3 Integrin," *J Biol Chem* 283:3224-30 (2008), which is hereby incorporated by reference in its entirety).

GPIIIa49-66 contains 6 negatively charged amino acids, 5 Glutamic acid and 1 Aspartic acid residue. It is therefore not surprising that there are many positively charged residues in the heavy and light chains of scFv antibodies and that the positively charged residues play a role in the platelet fragmentation by scFv antibodies.

Example 22

Effect of Active scFv-A11 on Mouse Ischemic Stroke

Figure 10:
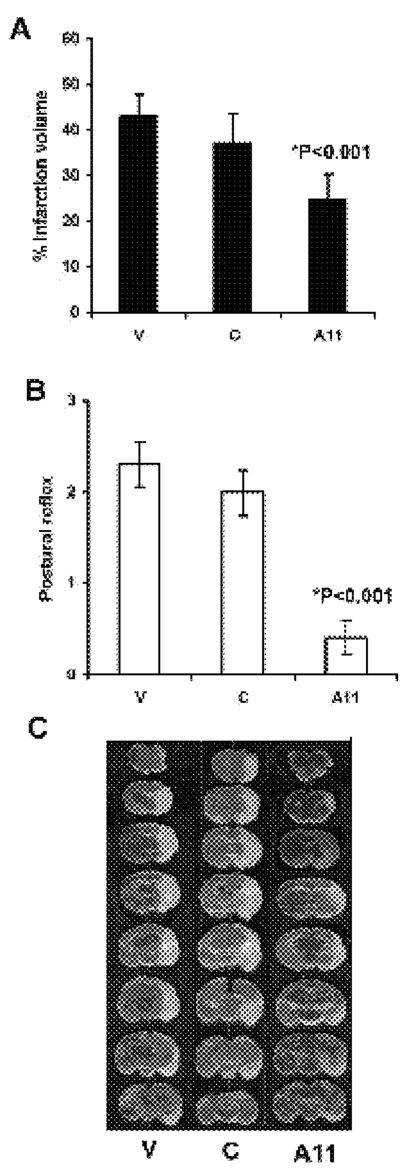
FIGS. 10A-C show data 2 hrs before or after obstruction of the right middle cerebral artery and 48 hrs after removal of obstruction.

To further examine the antithrombotic function of active scFv-A11 in vivo, the effect of 2 hrs after 90 min obstruction (followed by release) of the middle cerebral artery with scFv-A11 (20 μg/mouse) on the amelioration of mice ischemic stroke was analyzed. The results showed that scFv-A11 group had significantly smaller mean infarct volumes (FIG. 10A) and better sensorimotor behavior than the control group (FIG. 10B). Representative TTC stained sections from the three groups are shown in FIG. 10C.

Example 23

Genetic Modification of scFv-A11 Antibody

Figure 11:
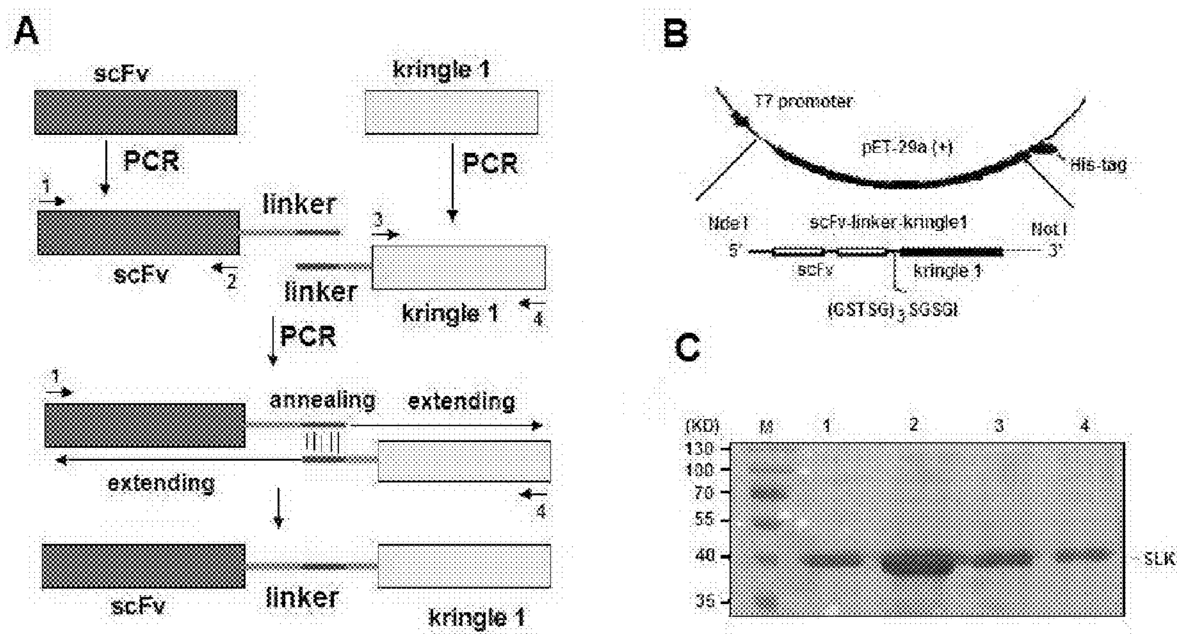
FIGS. 11A-C show the molecular design, cloning, and expression of bifunctional fusion protein scFv-A11-linker-kringle-1 (SLK).

Since fibrin is interspersed around platelet thrombi and $1^{st}$ kringle of plasminogen binds avidly to the lysine of partially degraded fibrin, a bifunctional fusion antibody including scFv-A11 and $1^{st}$ kringle (78aa, ~9 kD) was constructed which could localize (home in) to platelet thrombus with the active $1^{st}$ kringle and lyse platelets with scFv-A11 (FIG. 11A-B). Coomassie Blue-stained gel showed the predicted size of affinity purified scFv-A11-linker-kringle-1 (SLK) is ~40 kD under reduced condition by 12% SDS-PAGE gel (FIG. 11C).

Example 24

Cloning of scFv-A11 and scFv-A11-Linker-Kringle-1

The DNA of pIT2-A11 phagemid was used as a template for PCR with the sense primer 5'-CCATGGCCGAGGTGCAGCTG-3' (SEQ ID NO: 23) and the antisense primer 5'-CGGGCCGCACTCTTTGGTCC-3' (SEQ ID NO: 24). The restriction site Noc I was introduced by the sense primer and the restriction site Not I was introduced by the antisense primer. The PCR fragment digested with Noc I/Not I was ligated into double-digested pET29a vector (Noc I/Not I). The human pDNR-LIB (from ATCC, Cat No. 10468491) was used as plasminogen kringle-1 template for PCR with sense primer 5'-AGCTCATATGTGCAAGACTGGGAATG- GAAAG-3'(SEQ ID NO: 25) and the antisense primer 5'-TC-CTCTCGAGCTCAAGAATGTCGCAGTAGTC-3' (SEQ ID NO: 26). The restriction site Nde I was introduced by the sense primer and the restriction site Xho I was introduced by the antisense primer. The PCR fragment digested with Nde I/Xho I was ligated into double-digested pET29a vector (Nde I/Xho I). The ligated plasmid pET29a-scFv-A11 and pET29a-kringle-1 was then transformed into TOP10 *E. coli*, purified using Mini-Prep kits (Qiagen), and verified by sequencing.

To introduce the linker sequence between scFv-A11 and the kringle-1 domain from human plasminogen, the nucleotide sequence of the cassette scFv-Linker-kringle1 was generated by three-stage PCR. The first stage PCR fragment covered from the start codon of scFv to the middle half of the linker sequence. The sequence was generated by PCR using pET29a-scFv-A11 as template. The primers used for this amplification were SCFN 5'-GGAATTCCATATGGC-CGAGGTGCAGCTGTT-3' (SEQ ID NO: 27); SCFC 5'-AC-TAGTAGATCCACCACTTGTCGACCCAC-CAGAAGTACTTCCCCGTTTGAT TTCCACCTTGGTCC-3' (SEQ ID NO: 28). The resulting product was a 768-bp fragment with Nde I site at the 5' end. The second half of the expression cassette carried a sequence encoding the C-terminal half of the linker and the kringle-1 domain. This sequence was generated by the second PCR stage using pET29a-kringle-1 as template. The forward primer KRN 5'-CAAGTGGTGGATCTACTAGTG-GCTCTGGATCCGGAATTTGCAAGACTGGG AATG-GAAAG-3' (SEQ ID NO: 29) has three portions: the first 20 bp is the reverse complement sequence of part of the SCFC primer, the residual sequence encoded the sequence for the C-terminal half of the linker, and the beginning of the kringle-1 domain. The backward primer is KRC TAGGATC-CGCGGCCGCCTCAAGAATGTCGCAGTAGT (SEQ ID NO: 30). The resulting product was a 270 bp fragment with Not I site at the 3' end. The full-length scFv-A11-Linker-kringle-1 cassette was generated by the third PCR stage using the primers SCFN and KRC. The resulting 1038 bp Nde I-Not I fragment was digested by Nde I and Not I thereafter inserted into pET-29a to generate pET29a-scFv-A11-linker-kringle-1 (SLK).

Example 25

Refolding and Purification of Recombinant scFv-A11 Soluble Protein

Refolding and purification steps were performed at 4° C. Inclusion body pellets were prepared as described (Lamberski et al., "Expression and Purification of a Single-chain Variable Fragment Antibody Derived from a Poly-responsive Monoclonal Antibody," *Protein Expression and Purification* 47: 82-92 (2006), which is hereby incorporated by reference in its entirety). The pellets (from 3.3 g wet weight cells) were thawed on ice, dissolved in 20 ml MTN and 6 M GuHCl, and centrifuged for 15 min at 15,000 g to remove any insoluble material. The protein concentration was adjusted to 1 mg/ml, then drip-diluted 20-fold into refolding buffer (50 mM MES, pH 6.5; 10 mM NaCl; 550 mM GuHCl, 2 mM $MgCl_2$, and 0.025% Tween 20) at a rate of 0.4 ml supernatant/min and then slowly mixed with a magnetic stir bar for 15 min. The solution was centrifuged for 10 min at 15,000 g to remove any aggregated material. Ni-NTA agarose resin (1 ml packed resin/10 ml supernatant) was added to the refolded solution and allowed to mix for 1 hr. The solution was centrifuged for 5 min at 125 g to gently pellet the Ni-NTA agarose resin. The supernatant was decanted and the resin was added to a column. The resin was washed twice with 10 column volumes of wash buffer (50 mM MES, pH 6.5; 500 mM NaCl; 2 mM $MgCl_2$, 0.025% Tween 20; and 20 mM imidazole). The recombinant proteins were eluted from the column using washing buffer containing 500 mM imidazole. The protein was finally dialyzed in PBS, and the purity was checked by 12% SDS-polyacrylamide gel electrophoresis (SDS-PAGE).

Example 26

Comparison of scFv-A11 and Bifunctional Fusion Antibody

The binding specificity of scFv-A11 and bifunctional fusion antibody (SLK) on platelet and fibrin was evaluated by ELISA as described in methods. It was demonstrated that both scFv-A11 and SLK could bind to platelet GPIIIa(49-66) (FIG. 12A). These two antibodies induce platelet fragmentation at various concentration (6.3, 3.2, 1.6, 0.8 μM, respectively), whereas irrelevant scFv (13CG2) had no effect on platelet fragmentation (FIG. 12B). A representative ELISA study demonstrated that SLK retained fibrin binding ability compared to solo scFv-A11 (FIG. 12C).

Fibrin homing by the $1^{st}$ kringle of plasminogen allows for local enrichment of thrombolytic agents at the site of the thrombus at low systemic concentrations and thus decreases the risk of bleeding complications. Sufficient amount of fibrin is present even in platelet-rich thrombi.

Example 27

Effect of A11 and $1^{st}$ Kringle of Plasminogen on Carotid Artery Occlusion

Figure 12:
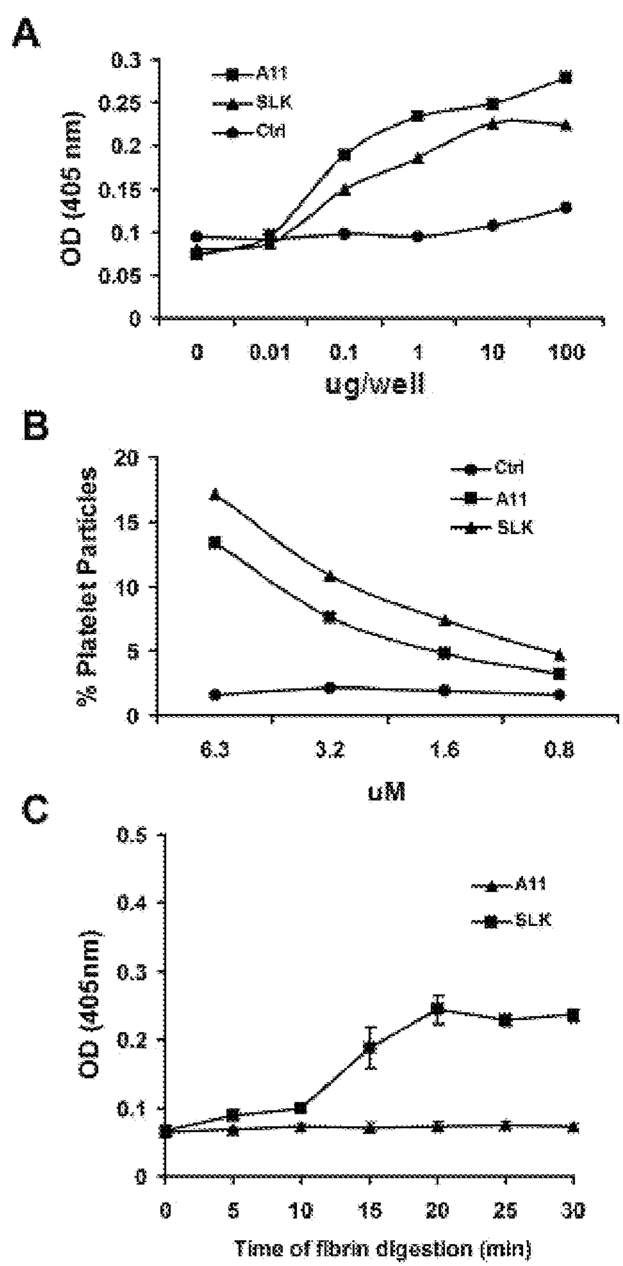
FIGS. 12A-C compare the scFv-A11 and bifunctional fusion antibody.

The $1^{st}$ kringle of plasminogen homes selectively to partially degraded fibrin interspersed within the platelet thrombus by forming a covalent bond with C-terminal lysines of fibrin (Fleury et al., "Characterization of the Binding of Plasminogen to Fibrin Surfaces: The Role of Carboxyterminal Lysines," *Biochemistry* 30:7630-8 (1991), which is hereby incorporated by reference in its entirety). The $1^{st}$ kringle of plasminogen is attached to scFv-A11 by employing a $(GSTSG)_3$ SGSGI (SEQ ID NO: 16) linker (FIG. 11A-B). Data reveal that the recombinant agent is effective in vitro (induces oxidative platelet fragmentation) and in vivo (reopens occluded carotid artery thrombus after 4 hrs of occlusion), whereas scFv-A11 has no effect at 4 hrs (FIG. 12).

Figure 13:
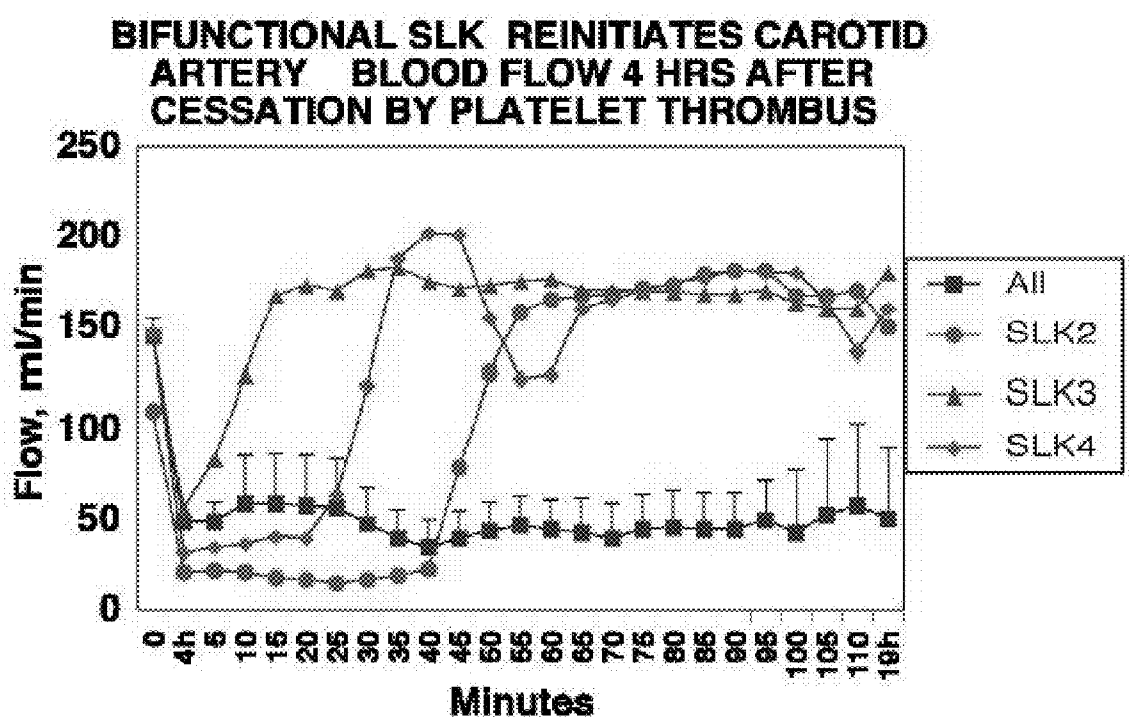
FIG. 13 shows the effect of bifunctional scFv-A11-linker-kringle-1 (SLK) on reinitiation of carotid artery flow after 4 hrs of thrombus inhibition of blood flow. i.v. infusion of A11 (25 μg/mouse) had no effect, n=4. SEM is given. SLK2 (25 μg/mouse) and SLK3 (37 μg/mouse) restored blood flow at 40 and 4 min respectively after 4 hrs of cessation of blow flow. SLK 4 (37 μg/mouse) restored blood flow at 20 min.

Bifunctional scFv-A11-plasminogen $1^{st}$ kringle agent (SLK) is more specific in that the plasminogen $1^{st}$ kringle covalently homes to newly deposited fibrin strands within and surrounding the platelet thrombus, avoiding any effect on non-activated circulating platelets. FIG. 13 demonstrates the advantage of this approach by the ability of this agent to reopen occluded carotid vessels 4 hrs after cessation of blood flow, whereas scFv-A11 alone had no effect at 4 hrs. FIG. 13 depicts the function of SLK compared to solo scFv-A11 antibody treatment.

A similar bifunctional agent in which scFv-A11 is directed toward activated platelets by its linkage to the monoclonal antibody heavy chain of PAC-1 could be similarly effective as SLK. Both agents at low doses could be synergistic with respect to their effect on platelet occlusion.

scFv-A11 not only prevents post-cerebral artery reperfusion thrombus, 2 hrs before occlusion ($t_{1/2}$ of 3½ hrs), but it is also effective 2 hrs after cessation of thrombus flow—with respect to cerebral infarct, neurologic damage and residual neurologic function—thus supporting a dynamic ongoing process of post-reperfusion occlusion.

Example 28

Figure 14:
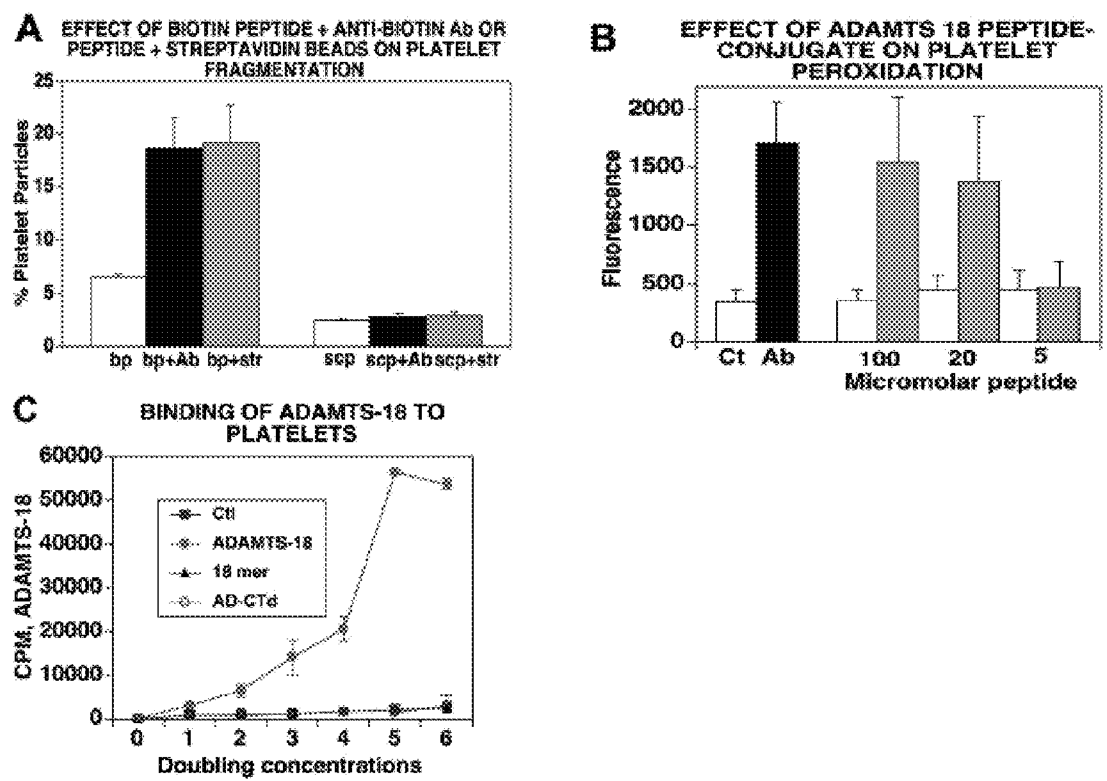
FIGS. 14A-C show the effect of ADAMTS-18 on oxidative platelet fragmentation and binding to platelets.

ADAMTS-18 C-Terminal Peptide Mimics the Effect of Antibody-Induced Platelet Oxidative Fragmentation In searching for a natural ligand to induce oxidative platelet fragmentation, the platelet GPIIIa(49-66) peptide was used as 'bait'. A phage surface display 7-mer peptide library was screened using the GPIIIa(49-66) peptide as bait in three rounds of washes, elutions, and amplification. Twenty clones were isolated. One of these clones, (VHCVQLY) (SEQ ID NO: 31) had 70% identity with ADAMTS-18 (1148-1152). An 18-mer peptide of ADAMTS-18 was, therefore, synthesized from the C terminal TSR motif and conjugated to Biotin, Bio-VQTRSVHCVQQGRPSSSC-OH (SEQ ID NO: 17). The peptide alone had no effect on platelet oxidative fragmentation. However, platelet fragmentation was obtained with the 18-mer Biotin-peptide plus an anti-Biotin antibody or with streptavidin beads, but not with the Biotin peptide alone (FIG. 14A). No effect was noted with a Biotin-labelled scrambled peptide Bio-VQTRSVQVHCQGRPSSSC-OH (SEQ ID NO: 18) plus anti-biotin antibody or streptavidin beads. Oxidation is shown in (FIG. 14B). These data suggest that β3 clustering is required and Fc receptor plays no role.

Example 29

Screening Phage Display Peptide Library for ADAMTS-18

The PhD-7 phage library was obtained from New England Biolabs (Cambridge, Mass. 02139). Biotin conjugated GPIIIa(49-66) peptide (13 ng) was incubated with $2\times10^{11}$ pfu phage in 400 μl TBST buffer (Tris 50 mM, NaCl 150 mM, Tween-20 0.1% pH 7.5) at 4° C. overnight. Positive phage clones were pulled down and washed with TBST by adding 20 μl avidin-agarose beads (Sigma-Aldrich, Mo. 63178). Phage clones with specific binding to GPIIIa(49-66) were eluted by adding 13 μg of non-biotin conjugated GPIIIa(49-66) in 200 μl TBST. The eluted phage was amplified in *E. coli* ER2738. The amplified phage were titered on LB/IPTG/X-gal plates and the titer, derived from the number of blue phage plaques, used to calculate an input volume corresponding to $2\times10^{11}$ pfu phages for the next round of panning After the third round of panning, 20 clones were randomly selected for sequencing. Phage peptide sequences were analyzed for sequence similarity to other proteins using the BLAST algorithm of the Blast program and the database of the National Center for Biotechnology Information (NCBI).

Example 30

Binding of ADAMTS-18 to Platelets

Formal proof of ADAMTS-18 or anti-GPIIIa(49-66) antibody reactivity against GPIIIa was obtained by utilizing platelets of GPIIIa−/− knock out mice. Neither ADAMTS-18 nor anti-GPIIIa(49-66) antibody fragmented GPIIIa−/− platelets (n=2). Further proof of binding to platelets was obtained with $^{35}$S-ADAMTS-18 binding studies. FIG. 14C demonstrates saturation binding of ADAMTS-18, inhibited by the 18 mer peptide. No binding was noted with a control $^{35}$S-luciferase protein or with a C-terminal truncated $^{35}$S-ADAMTS-18. Similar results were obtained with an ADAMTS-18 385aa fragment (AD-18F).

Example 31

Effect of Truncated ADAMTS-18 on Platelet Fragmentation

A C-terminal fragment of ADAMTS-18 might be the operational end for platelet oxidative fragmentation, because ADAMTS-18 binds to GPIIIa(49-66) by its 18-mer moiety located in the C terminal region, ADAMTS-18 oxidative activity can be inhibited by an scFv antibody directed against the 18-mer and thrombin cleavage could expose a C-terminal functional fragment. Accordingly, 3 truncated fragments within the C-terminal 4 TSR motifs were cloned in an *E. coli* expression vector pGEX-4T-2 (FIG. 15A). FIG. 15B demonstrates that the ADAMTS-18 385 amino acid (aa) fragment (837-1221) (AD-18F), encompassing the 4 TSR motifs (containing the GPIIIa binding site), fragmented platelets at varying dilutions, starting at n(neat)=1.3 μM. The ADAMTS-18 188 amino acid structure (1034-1221) was considerably less potent with no platelet fragmentation at 1.3 μM and partial activity at n=19 μM. The small ADAMTS-18 66 amino acid structure (1156-1221) not containing the GIIIa binding site was inactive at n=85 μM. Both fragmentation and oxidation induced by the 385 aa fragment were inhibited by DPI and catalase (FIGS. 15C and D), as previously reported for anti-GPIIIa(49-66) antibody (Nardi et al., "Complement-independent Ab-induced Peroxide Lysis of Platelets Requires 12-lipoxygenase and a Platelet NADPH Oxidase Pathway," *J Clin Invest* 113:973-980 (2004); Nardi et al., "Complement-independent, Peroxide Induced Antibody Lysis of Platelets in HIV-1-related Immune Thrombocytopenia," *Cell* 106:551-561 (2001), which are hereby incorporated by reference in their entirety). Similar results were obtained with apocynin for fragmentation and oxidation with an ~IC50 of 30 μM, n=3.

Proof of ADAMTS-18 induced platelet fragmentation was further obtained by measurement of LDH release into the supernatant at 0-240 min. LDH at 0 time was 10±1 μ/L which increased 83 fold at 60 min and 241 and 260 fold at 120 and 240 min, respectively. Similar results were obtained with anti-GPIIIa(49-66) antibody, confirming previous studies (Nardi et al., "Complement-independent, Peroxide Induced Antibody Lysis of Platelets in HIV-1-related Immune Thrombocytopenia," *Cell* 106:551-561 (2001), which is hereby incorporated by reference in its entirety).

Example 32

Recombinant ADAMTS-18 385aa Fragment (AD-18F) Destroys Platelet Aggregates

In considering a possible mechanism for C-terminal ADAMTS-18 induced platelet oxidative fragmentation, it became evident that this C-terminal ADAMTS-18 could represent a physiologic clearing agent for the dissolution of platelet thrombi on activated endothelium. To test this collagen—as well as ADP-induced platelet aggregates in the presence of fibrinogen were prepared and platelet-fibrinogen aggregates of ~30 and ~10 platelets/aggregates were obtained, respectively. FIG. 5A demonstrates that both anti-GPIIIa(49-66) antibody and the ADAMTS-18 385aa (AD-18F) fragment disaggregate collagen-induced platelet clumps to the same extent, with nadir at 2 hr, whereas the scrambled ADAMTS-18 385aa or the 66aa fragment did not. Similar results were obtained with ADP aggregates with nadir at 4-8 hr. To determine whether decreased aggregate size was a function of disaggregation or platelet destruction or both, LDH release into the media was assayed. As could be predicted from previous experiments which described antibody-induced oxidative platelet fragmentation in vitro with LDH release, similar results were obtained with ADAMTS-18 measurements of LDH release as an indicator of platelet lysis. With collagen-induced platelet aggregates, LDH release increased 215 fold, above background. FIG. 5B shows a photomicrograph of platelet aggregate destruction by ADAMTS-18 386 aa fragment (AD-18F) as compared to control. Thus, the AD-18F fragment induces platelet aggregate destruction.

Example 33

Recombinant ADAMTS-18 385 aa (AD-18F) Fragment Reacts More Strongly with TFLLRN-Activated Platelets Activated platelets have more GPIIb-IIIa reactive receptors on their surface, therefore the 385 aa fragment AD-18F reacts more avidly with platelets pretreated with the thrombin receptor against TFLLRN (SEQ ID NO: 7). FIG. 5C demonstrates this to be the case. TFLLRN-activated platelets particularly at low AD-18F concentration have ~22 fold greater sensitivity. Similar results were obtained with thrombin as well as anti-GPIIIa(49-66) antibody.

Example 34

Anti-ADAMTS-18 Antibody Shortens the Bleeding Time

Since the ADAMTS-18 385 aa (AD-18F) fragment appears to be a negative regulator of platelet aggregate stability, an antibody against ADAMTS-18 18-mer peptide should shorten the bleeding time. FIG. 5D demonstrates a dramatic 4.5 fold shortening of the mouse tail vein bleeding time 60 min after i.v. injection of 10 μg of rabbit anti-ADAMTS-18 IgG. Preimmune IgG had no effect, (3.6±0.65 vs 0.8±0.04 min respectively), p=0.002, n=10. These data support the conclusion that C-terminal ADAMTS-18 is a negative regulator of platelet aggregate stability.

Example 35

Effect of ADAMTS-18 385 aa (AD-18F) Fragment on Carotid Artery Platelet Thrombus Formation This in vivo experiment directly assesses the effect of ADAMTS-18 385 aa fragment (AD-18F) on arterial platelet thrombus induced with $FeCl_3$. FIG. 6A demonstrates a ~3 fold prevention of carotid artery platelet thrombus formation as measured by carotid artery blood flow. FIG. 6B depicts the SEM at 5 minute intervals. Differences are statistically significant at 20-35 min, p<0.05, Student t test.

Example 36

Effect of Anti-GPIIIa(49-66) scFv-A11 Fragment and ADAMTS-18 385 aa (AD-18F) Fragment on Post Ischemic Cerebral Stroke This experiment studies an experimental cerebral stroke model induced by ischemia of the middle cerebral artery. Both A11 and AD-18F (t½ of 3½ hrs) can prevent (2 hrs before occlusion) as well as ameliorate (2 hrs after occlusion) murine middle cerebral artery stroke and neurologic damage (Tables 1 and 2), thus supporting a dynamic ongoing process of 'post-reperfusion occlusion'. Table 2 demonstrates ~50% protection of infarction and functional neurologic damage by ADAMTS-18 385 amino acid (aa) fragment (AD-18F).

TABLE 1

Anti-GPIIIa(49-66) scFv-A11, 8 Days After Removal of Obstruction

| | N | % Infarction | P | Cavitation | P | Postural Reflex+ | P | Rotor Rod$ | P | Traverse Beam§ | P |
|---|---|---|---|---|---|---|---|---|---|---|---|
| Post All | 9 | 24.8 ± 5.5 | 0.002 | 1.52 ± 1.0 | 0.01 | 0.41 ± 0.18 | 0.0002 | 4.98 ± 0.28 | 0.003 | 6.96 ± 0.037 | 0.0023 |
| Pre All | 9 | 25.5 ± 6.0 | 0.0002 | 4.64 ± 1.7 | 0.0015 | 0.82 ± 0.25 | 0.0081 | 3.94 ± 0.36 | 0.038 | 6.33 ± 0.39 | 0.049 |
| Saline | 14 | 43.0 ± 4.8 | | 9.98 ± 1.9 | | 2.31 ± 0.25 | | 3.19 ± 0.34 | | 4.52 ± 0.46 | |
| Control IgG | 5 | 37.2 ± 6.2 | | 8.80 ± 2.1 | | 2.00 | | 3.43 | | 5.45 | |

P* Student t test comparison of saline vehicle vs i.v. injection of 25 μg of scFv A11 Ab or scFv control IgG (Ctl IgG) 2 hrs pre or 2 hrs post obstruction and release of right middle cerebral artery.
SEM is given.
+Postural Reflex - higher number reflects greater neurologic impairment.
$Rotor Rod and §Transverse Beam - lower number reflects neurologic impairment.
No microscopic hemorrhage seen.

TABLE 2

ADAMTS-18 385AA Fragment Given 2 hrs Before or After Obstruction of Right Middle Cerebral Artery and Examined 8 days After Removal of Obstruction

| | N | % Infarct | Postural Reflex+ | Rotor Rod$ | Traverse Beam§ |
|---|---|---|---|---|---|
| 385AA | 13 | 23.9 ± 4.0 | 1.02 ± 0.17 | 4.62 ± 0.58 | 5.97 ± 0.48 |
| 66AA | 8 | 43.8 ± 7.3 | 2.87 ± 0.13 | 3.23 ± 0.45 | 3.87 ± 0.90 |
| Saline | 14 | 43.0 ± 4.8 | 2.31 ± 0.25 | 3.19 ± 0.34 | 4.52 ± 0.46 |
| P* | | <0.001 | <0.002 | <0.04 | <0.01 |

P* refers to Student test comparison of i.v. injections of saline vehicle vs 35 μg of ADAMTS-18 385AA Fragment vs functionally inactive ADAMTS-18 66AA Fragment (control).
+Postural Reflex - higher number reflects greater neurologic impairment.
$Rotor Rod and §Transverse Beam - lower number reflects neurologic impairment.

Protection was obtained if AD-18F (or antibody) were given 2 hrs before or 2 hrs after 90 min obstruction followed by release of the middle cerebral artery. No bleeding was observed. Platelet counts remained within 90% of normal range at 4 hr following AD-18F vs control injection ($1.0\times10^6$ vs $0.9\times10^6$ μl, respectively, n=4). ADP, collagen or TFLLRN (SEQ ID NO: 7)-induced platelet aggregation in vitro was unaffected. These data indicate that ADAMTS-18 can regulate ischemic cerebral stroke without bleeding.

Example 37

Bifunctional A11-PAC-1 Agent

PAC-1 is an IgM monoclonal antibody which binds to activated platelets—particularly to conformational changes in GPIIb-GPIIIa. A11 has been successfully linked to the heavy-light chain variable binding region of PAC-1 (APAC) in a similar fashion as with SLK. The amino-acid sequence of the variable heavy and light chains have been published in Abrams et al., "A Baculovirus-expressed Antibody Fab Fragment Binds Selectively to the Activated Form of Integrin αIIbβ3," *J Biol Chem* 269:18781-8 (1994), which is hereby incorporated by reference in its entirety. The cDNA was produced from this heavy and light chain variable region with a $(G45)_3$ linkage to produce an scFv-PAC-1 and then linked this combined single heavy-light chain to A11 with $(GSTSG)_3$ SGSGI, to produce an scFv-A11-PAC-1 bifunctional agent. The amino acid sequence for the scFv-A11-PAC-1 bifunctional agent (516 aa) is as follows (SEQ ID NO: 32), linker sequence is underlined:

```
  1 MAEVQLLESG GGLVQPGGSL RLSCAASGFT FSSYAMSWVR QAPGKGLEWV SSITSTGMET

 61 RYADSVKGRF TISRDNSKNT LYLQMNSLRA EDTAVYYCAK GKSHFDYWGQ GTLVTVSSGG

121 GGSGGGGSGG GGSTDIQMTQ SPSSLSASVG DRVTITCRAS QSISSYLNWY QQKPGKAPKL

181 LIYTASFLQS GVPSRFSGSG SGTDFTLTIS SLQPEDFATY YCQQRKSYPR TFGQGTKVEI

241 KRGSTSGGST SGGSTSGSGS GIQVQLKQSG PGLVQPSQSL SITCTVSGFS LTSYGVHWVR

301 LSPGKGLEWL GVIWSGGSTD YNAAFISRLS ISKDNSKSQV FFKMNSLQAN DTGIYYCARR

361 SPSYYRYDGA GPYYAMDYWG GGTSVTVSSG GGGSGGGGSG GGGSDVLMTQ TPLSLPVSLG

421 DGASISCRSS QSIVHSNGNT YLEWYLQKPG GSPKLLIYKV SNRFSGVPDR FTGSGSGTDF

481 TLKISRVEAE DLGVYYCWGG SHVPYTFGGG TKLEIK
```

The published RYD binding region is substituted with RGD for possible greater integrin binding. Recombinant APAC fragments platelets following 4 hrs of incubation at 37° C. and appears to be ~2 fold more potent in vitro than SLK on a molar basis. APAC has a minimal effect on platelet count (~10% decrease). It has been successfully tested in the ex vivo collagen-induced platelet aggregate system (FIG. 16), and will be tested in the in vivo carotid artery thrombus model as well as in the cerebral stroke model. Comparison of its biological activity to SLK will determine whether there may be a synergistic effect at less than optimal single agent concentrations. This will not only lead to a more potent anti-platelet-thrombolytic agent, but also avoid any toxicities from either single agent, at highest concentrations.

The blockade of platelet glycoprotein IIb/IIIa receptor is extremely valuable in interventional cardiology, because platelet-rich rather than fibrin-rich thrombosis is responsible for many acute complications of angioplasty. Currently, three types of anti-platelet integrin antibodies specific for αIIb or $\beta_3$ are described in the literature: (a) with no effect on platelet aggregation (PMI-1, αIIb-specific) (Ginsberg et al., "Divalent Cation Regulation of the Surface Orientation of Platelet Membrane Glycoprotein IIb. Correlation with Fibrinogen Binding Function and Definition of a Novel Variant of Glanzmann's thrombasthenia," *J Clin Invest* 78:1103-1111 (1986) and Shadle et al., "Platelet-collagen Adhesion. Inhibition by a Monoclonal Antibody That Binds Glycoprotein IIb," *J Cell Biol* 99:2056-2060 (1984), which are hereby incorporated by reference in their entirety); (b) with inhibition of platelet aggregation (anti-LIBS-1, $\beta_3$-specific) (Frelinger et al., "Selective Inhibition of Integrin Function by Antibodies Specific for Ligand-occupied Receptor Conformers," *J Biol Chem* 265:6346-6352 (1990), which is hereby incorporated by reference in its entirety); and (c) with activation of $\alpha II_b\beta_3$ (D3GP3, anti-LIBS-2, -3, -6, $\beta_3$-specific) (Frelinger et al., "Selective Inhibition of Integrin Function by Antibodies Specific for Ligand-occupied Receptor Conformers," *J Biol Chem* 265:6346-6352 (1990); Kouns et al., "A Conformation-dependent Epitope of Human Platelet Glycoprotein," *J Biol Chem* 265:20594-20601 (1990); and Frelinger et al., "Monoclonal Antibodies to Ligand-Occupied Conformers of Entegrin $\alpha II_b\beta_3$ (Platelet Glycoprotein GPIIb-IIIa) Alter Receptor Affinity, Specificity and Function," *J Biol Chem* 266:17106-17111 (1991), which are hereby incorporated by reference in their entirety). A human monoclonal antibody against platelet integrin GPIIIa(49-66) named scFv-A11 is unique, because it can reopen large platelet thrombi by inducing oxidative platelet thrombi fragmentation.

Integrin GPIIIa(49-66) (CAPESIEFPVSEAREVLED) (SEQ ID NO: 9) contains 6 negatively charged amino acids, 5 glutamic and 1 aspartic acid. It is, therefore, not surprising that there are many positively charged amino acids (Arg, Lys, and His) in the CDRs of both heavy and light chains of scFv-A11 antibody. Compared with other anti-$\alpha II_b\beta_3$ antibodies, the scFv-A11 antibody does not contain RGD sequences so, it is unlikely that this antibody can cross react with the RGD binding site of $\alpha II_b\beta_3$ integrin. There are several major advantages of scFv-A11.

Firstly, the antibody could fragment/disaggregate platelet thrombi and relieve ischemic stroke. More importantly, no bleeding complications were observed in tested animals using treatment doses. Therefore, reopening larger arterial platelet thrombi with specific anti-GPIIIa(49-66) scFv-Ab can be of clinical value.

Secondly, the antibody can be used to prevent early plug formation via the lysis of surrounding platelets, since the recently reported finding that the initial thrombus formation after vessel injury can be mediated by nonactivated platelets (Furie et al., "Thrombus Formation in vivo," *J Clin Invest* 115:3355-3362 (2005), which is hereby incorporated by reference in its entirety).

Thirdly, the antibody is human antibody. This will help to lessen HAMA (human anti-mouse antibody) response. In addition, since it is scFv antibody that lacks the Fc region, it will, therefore, not induce complement activation and the phagocytic/cytokine response in patients.

Fourthly, the small size of scFv makes it penetrate tissues more easily than the full length antibody.

Additional advantages can be provided by the scFv format, which is currently entering the phase of clinical trials (Fitch et al., "Pharmacology and Biological Efficacy of a Recombinant, Humanized, Single-chain Antibody C5 Complement Inhibitor in Patients Undergoing Coronary Artery Bypass Graft Surgery with Cardiopulmonary Bypass," *Circulation* 100:2499-2506 (1999) and Leath et al., "Single-chain Antibodies: A Therapeutic Modality for Cancer Gene Therapy (Review)," *Int J Oncol* 24:765-771 (2004), which are hereby incorporated by reference in their entirety). The ease of cloning in bacteria offers the opportunity of genetic engineering, such as further optimization and construction of fusion molecules (Peter et al., "Construction and Functional Evaluation of a Single-chain Antibody Fusion Protein with Fibrin Targeting and Thrombin Inhibition After Activation by Factor Xa," *Circulation* 101:1158-1164 (2000), which is hereby incorporated by reference in its entirety). In contrast to the production of antibodies in hybridoma or other mammalian cells, scFv antibodies can be produced in bacteria at low cost and are easily amenable to commercial scale up. Another technical advantage is the possibility of adding functional groups (eg. His-tag) to allow for high-purity production using affinity columns.

Fibrin targeting allows for local enrichment of thrombolytic agents at the site of the thrombus at low systemic concentrations and thus decreases the risk of bleeding complications. Sufficient amount of fibrin are present even in platelet-rich thrombi. The bifunctional fusion protein of the present invention can contain both scFv anti-GPIIIa(49-66) antibody and fibrin targeting molecule kringle-1 that is capable of disrupting platelet aggregate by homing to the platelet arterial thrombus. In summary, this unique single-chain antibody can reopen platelet thrombi by disaggregating platelet thrombi. It provides a different clinical approach to reopen arterial platelet thrombi.

Anti-GPIIIa(49-66) scFv-A11 has the ability to reverse $FeCl_3$ induced occlusion of the artery 2 hr after cessation of blood flow. Similar protection was noted in a post-ischemic middle cerebral artery stroke model in which ADAMTS-18 385 aa fragment (AD-18F) significantly prevented and protected against infarction and neurologic damage by ~50%. ADAMTS-18, 385 aa fragment (AD-18F) is also capable of: 1) dissolving platelet aggregates produced ex vivo with fibrinogen and collagen or ADP; 2) regulating the in vivo bleeding time; 3) protecting against $FeCl_3$ induced carotid artery thrombus formation; and 4) protecting against post-ischemic cerebral infarction. This supports a physiologic and/or therapeutic role for ADAMTS-18 in hemostasis. ADAMTS-18 is a natural ligand, which binds to platelet integrin GPIIIa(49-66) by its 18 mer C-terminal end and induces oxidative-platelet fragmentation and platelet thrombus destruction, following thrombin cleavage.

ADAMTS-18 protein can operate in the absence of its metalloproteinase domain through a C-terminal 18-mer fragment binding site. Various recombinant truncated constructs of ADAMTS-18 were synthesized at its C-terminal region. One such C-terminal fragment containing 385 amino acids (aa) and 4 TSR motifs is capable of inducing the same platelet oxidative-fragmentation reaction, as substantiated by its inhibition with catalase and DPI.

Thrombin induces platelet thrombus formation and endothelial cell activation. Platelet thrombus formation is a dynamic process in which platelets are deposited and released from the endothelial surface depending upon an equilibrium between endothelial injury and thrombus dissolution (regulation). Thrombin-induced endothelial cell activation stimulates the secretion of HUVEC ADAMTS-18 which binds to platelet GPIIIa(49-66). Thrombin cleaves ADAMTS-18 to produce the active 45 kD C-terminal fragment which clusters β3. Clustering could be due to interchain disulfide bridging, because this fragment is enriched with cysteine. Clustering induces 12(S)-HETE production which regulates thrombus size by inducing oxidative fragmentation. Neutralization of thrombin by natural inhibitors halts thrombin-induced ADAMTS-18 release, preventing further platelet destruction. The degree of thrombus/platelet destruction is dependent upon the local platelet-endothelial concentration of ADAMTS-18 as well as the half-life of 12(S)-HETE and the C-terminal ADAMTS-18 in vivo. It is unlikely that the local ADAMTS-18 secreted by HUVEC would have any appreciable effect on circulating platelets or their function, because a 60 fold higher concentration employed for mouse clinical studies had no effect on platelet count. It is likely that ADAMTS-18 has a greater effect on thrombin-activated platelets in vivo (within the platelet thrombus) than inactivated platelets in the circulation.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A therapeutic agent comprising:

a GPIIIa(49-66)-specific targeting agent, said GPIIIa(49-66)-specific targeting agent being selected from the group consisting of a single chain anti-GPIIIa(49-66) antibody having the amino acid sequence of SEQ ID NO: 13, an ADAMTS-18 protein having the amino acid sequence of SEQ ID NO: 11, and binding portions thereof and a thrombi-specific homing agent linked to said GPIIIa(49-66)-specific targeting agent, said thrombi-specific homing agent being selected from the group consisting of 1st kringle of plasminogen, PAC-1 antibody, and antibody against P-selectin.

2. The therapeutic agent according to claim 1, wherein said GPIIIa(49-66)-specific targeting agent is A11, a single chain anti-GPIIIa(49-66) antibody, having the amino acid sequence of SEQ ID NO: 13.

3. The therapeutic agent according to claim 1, wherein said GPIIIa(49-66)-specific targeting agent is AD-18F polypeptide, a binding portion of ADAMTS-18 protein, having the amino acid sequence of SEQ ID NO: 10.

4. The therapeutic agent according to claim 1 further comprising:

a linker connecting said GPIIIa(49-66)-specific targeting agent and said thrombi-specific homing agent.

5. The therapeutic agent according to claim 4, wherein the linker connecting said GPIIIa(49-66)-specific targeting agent and said thrombi-specific homing agent has the amino acid sequence of $(GSTSG)_3$ SGSGI (SEQ ID NO: 16).

6. A therapeutic composition comprising:

the therapeutic agent of claim 1 and a pharmaceutically acceptable carrier.

7. A method of treating thromboembolic disorders in a subject, said method comprising:

administering the therapeutic agent of claim 1 to a subject under conditions effective to treat thromboembolic disorders in the subject.

8. The method according to claim 7, wherein said GPIIIa (49-66)-specific targeting agent is A11, a single chain anti-GPIIIa(49-66) antibody, having the amino acid sequence of SEQ ID NO: 13.

9. The method according to claim 7, wherein said GPIIIa (49-66)-specific targeting agent is AD-18F polypeptide, a binding portion of ADAMTS-18 protein, having the amino acid sequence of SEQ ID NO: 10.

10. The method according to claim 7 further comprising:

a linker connecting said GPIIIa(49-66)-specific targeting agent and said thrombi-specific homing agent.

11. The method according to claim 10, wherein the linker connecting said GPIIIa(49-66)-specific targeting agent and said thrombi-specific homing agent has the amino acid sequence of $(GSTSG)_3$ SGSGI (SEQ ID NO: 16).

12. The method of claim 7 further comprising:

selecting a subject with a thromboembolic disorder, wherein the therapeutic agent is administered to the selected subject.

13. The method of claim 7, wherein the thromboembolic disorder is selected from the group consisting of ischemic heart disease, stroke, arterial thrombosis, and pulmonary embolism.

14. The method of claim 7, wherein said administering is carried out parenterally, intravenously, intramuscularly, intraperitoneally, transdermally, or orally.

15. A method of inducing platelet fragmentation in a subject, said method comprising:

administering the therapeutic agent of claim 1 to a subject under conditions effective to induce platelet fragmentation in the subject.

16. The method according to claim 15, wherein said GPIIIa (49-66)-specific targeting agent is A11, a single chain anti-GPIIIa(49-66) antibody, having the amino acid sequence of SEQ ID NO: 13.

17. The method according to claim 15, wherein said GPIIIa (49-66)-specific targeting agent is AD-18F polypeptide, a binding portion of ADAMTS-18 protein having the amino acid sequence of SEQ ID NO: 10.

18. The method according to claim 15 further comprising:

a linker connecting said GPIIIa(49-66)-specific targeting agent and said thrombi-specific homing agent.

19. The method according to claim 18, wherein the linker connecting said GPIIIa(49-66)-specific targeting agent and said thrombi-specific homing agent has the amino acid sequence of $(GSTSG)_3$ SGSGI (SEQ ID NO: 16).

20. The method according to claim 15 further comprising:

selecting a subject with need to induce platelet fragmentation, wherein the therapeutic agent is administered to the selected subject.

21. The method according to claim 15, wherein said administering is carried out parenterally, intravenously, intramuscularly, intraperitoneally, transdermally, or orally.

* * * * *